(12) United States Patent
Park et al.

(10) Patent No.: US 11,298,344 B2
(45) Date of Patent: Apr. 12, 2022

(54) COMPOSITION FOR INHIBITING SODIUM LEAK CHANNEL (NALCN), COMPRISING N-BENZHYDRYL QUINUCLIDINE DERIVATIVES

(71) Applicant: Research & Business Foundation Sungkyunkwan University, Suwon-si (KR)

(72) Inventors: Myoung Kyu Park, Suwon-si (KR); Hyun Jin Kim, Suwon-si (KR); Suyun Hahn, Suwon-si (KR); So Woon Kim, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 16/392,680

(22) Filed: Apr. 24, 2019

(65) Prior Publication Data
US 2020/0016132 A1  Jan. 16, 2020

(30) Foreign Application Priority Data
Jul. 10, 2018  (KR) .......................... 10-2018-0080227

(51) Int. Cl.
*A61K 31/44* (2006.01)
*A61K 31/439* (2006.01)
*A61P 25/00* (2006.01)

(52) U.S. Cl.
CPC ............ *A61K 31/439* (2013.01); *A61P 25/00* (2018.01)

(58) Field of Classification Search
CPC .................................................. A61K 31/439
(Continued)

(56) References Cited

U.S. PATENT DOCUMENTS 5,807,867 A * 9/1998 Ito .................. C07D 453/02
514/305
2008/0132538 A1  6/2008 Chappell et al.
(Continued)

FOREIGN PATENT DOCUMENTS

WO   WO 2009/109001 A1   9/2009

OTHER PUBLICATIONS

Johnson et al. "The therapeutic potential of targeting substance P/NK-1R interaction in inflammatory CNS disorders," Frontiers in Cellular Neuroscience, 2017, vol. 10, Article 296. (Year: 2017).*
(Continued)

*Primary Examiner* — Shengjun Wang
(74) *Attorney, Agent, or Firm* — NSIP Law

(57) ABSTRACT

A composition for inhibiting sodium leakage channel (NALCN), including as an active ingredient N-benzhydryl quinuclidine (NBQN) or a N-benzhydryl quinuclidine derivative represented by the following Formula 1, wherein in the following Formula 1, R is an unsubstituted or substituted benzyl group

[Formula 1]

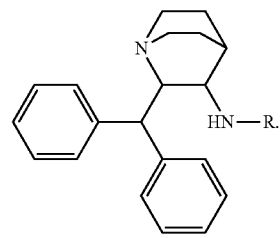

14 Claims, 14 Drawing Sheets

Specification includes a Sequence Listing.

(58) Field of Classification Search
USPC .......................................... 514/305; 424/439
See application file for complete search history.

(56) References Cited

U.S. PATENT DOCUMENTS

2009/0280159 A1* 11/2009 Paulsen ................ A61K 9/0056
424/439
2016/0324881 A1* 11/2016 Bergmann ......... A61K 31/5377

OTHER PUBLICATIONS

Croot et al. "Phonological and Articulatory impairment in Alzheimer's disease: A case series," Brain and Language, 2000, vol. 75, pp. 277-309 (Year: 2000).*
Ford et al. "Substance P-activated Na+ leak conductance enhances the intrinsic excitability of rodent spino-parabrachial projection neurons," Journal of Pain, Apr. 2017, vol. 18, No. 4, supplement, S22 (Year: 2017).*
Basar Delay of cognitive gamma response in Alzheimer's disease, NeuroImage: Clincial, 2016, vol. 11, pp. 106-115 (Year: 2016).*
Maud Cochet-Bissuel et al., "The sodium leak channel, NALCN, in health and disease," Frontiers in Cellular Neuroscience, May 20, 2014, vol. 8, Article 132, (17 pages in English).
Annika Thorsell et al., "Neurokinin-1 receptors (NK1R:s), alcohol consumption, and alcohol reward in mice," Psychopharmacology, 2010, vol. 209, pp. 103-111.
Barker, R., et al., "Substance P and multiple sclerosis." Medical hypotheses, 37, 1, 1992 (pp. 40-43).
Michaels, Lisa A., et al., "Serum Levels of Substance P are Elevated in Patients with Sickle Cell Disease and Increase Further during Vaso-Occlusive Crisis." Blood, The Journal of the American Society of Hematology, 92, 9, 1998 (pp. 3148-3151).
Fiebich, Bernd L., et al. "The Neuropeptide Substance P Activates p38 Mitogen-Activated Protein Kinase Resulting in IL-6 Expression Independently from NF-κB." The Journal of Immunology, 165, 10, 2000 (pp. 5606-5611).
Marriott, Ian et al., "IL-4 and IFN-γ Up-Regulate Substance P Receptor Expression in Murine Peritoneal Macrophages." The Journal of Immunology, 165, 1, 2000 (pp. 182-191).
Lallemend, François, et al., "Substance P protects spiral ganglion neurons from apoptosis via PKC-Ca2+-MAPK/ERK pathways." Journal of neurochemistry, 87, 2, 2003 (pp. 508-521).
Koon, Hon-Wai, et al., "Substance P-Stimulated Interleukin-8 Expression in Human Colonic Epithelial Cells Involves Protein Kinase Cδ Activation." Journal of Pharmacology and Experimental Therapeutics, 314, 3, 2005 (pp. 1393-1400).
Ikeda, Yoshiki, et al., "Administration of substance P during a primary immune response amplifies the secondary immune response via a long-lasting effect on CD8+ T lymphocytes." Archives of dermatological research, 299, 7, Jul. 21, 2007 (pp. 345-351).
Lu, Boxun, et al. "The Neuronal Channel NALCN Contributes Resting Sodium Permeability and Is Required for Normal Respiratory Rhythm." Cell, 129, 2, 2007 (pp. 371-383).
Lu, Boxun, et al., "Peptide neurotransmitters activate a cation channel complex of NALCN and UNC-80." Nature, 457, 7230, 2009 (pp. 741-744).
Swayne, Leigh Anne, et al., "The NALCN ion channel is activated by M3 muscarinic receptors in a pancreatic β-cell line." EMBO reports, 10, 8, 2009 (pp. 873-880).
Wang, Ke-Sheng, et al., "A genome-wide meta-analysis identifies novel loci associated with schizophrenia and bipolar disorder." Schizophrenia research, 124, 1-3, Sep. 7, 2010 (pp. 192-199).
Lu, Boxun, et al., "Extracellular Calcium Controls Background Current and Neuronal Excitability via an UNC79-UNC80-NALCN Cation Channel Complex." Neuron, 68, 3, Nov. 4, 2010 (pp. 488-499).
Swayne, Leigh Anne, et al., "The NALCN ion channel is a new actor in pancreatic β-cell physiology." Islets, 2, 1, 2010 (pp. 54-56).

Chu, John MT, et al., "Neuroprotective effects of neurokinin receptor one in dopaminergic neurons are mediated through Akt/PKB cell signaling pathway." Neuropharmacology, vol. 61, Issue 8, Dec. 2011 (pp. 1389-1398).
Ren, Dejian. "Sodium Leak Channels in Neuronal Excitability and Rhythmic Behaviors." Neuron, 72, 6, 2011 (pp. 899-911).
Balaban, Hatice, et al., "A Novel Locus for Restless Legs Syndrome on Chromosome 13q." European neurology, 68, 2, Jul. 10, 2012 (pp. 111-116).
Al-Sayed, Moeenaldeen D., et al., "Mutations in NALCN Cause an Autosomal-Recessive Syndrome with Severe Hypotonia, Speech Impairment, and Cognitive Delay." The American Journal of Human Genetics, 93, 4, 2013 (pp. 721-726).
Köroğlu, Çiğdem et al., "Recessive truncating NALCN mutation in infantile neuroaxonal dystrophy with facial dysmorphism." Journal of medical genetics, 50, 8, 2013 (pp. 515-520).
Cochet-Bissuel, Maud, et al., "The sodium leak channel, NALCN, in health and disease." Frontiers in cellular neuroscience, 8, May 20, 2014 (pp. 1-17).
Mok, Kin Y., et al., "Genomewide Association Study in Cervical Dystonia Demonstrates Possible Association with Sodium Leak Channel." Movement Disorders, 29, 2, 2014 (pp. 245-251).
Patro-Malysza, Jolanta, et al., "The Impact of Substance P on the Pathogenesis of Insulin Resistance Leading to Gestational Diabetes." Current pharmaceutical biotechnology, 15, 1, 2014 (pp. 32-37).
Chong, Jessica X., et al., "De Novo Mutations in NALCN Cause a Syndrome Characterized by Congenital Contractures of the Limbs and Face, Hypotonia, and Developmental Delay." The American Journal of Human Genetics, 96, 3, 2015 (pp. 462-473).
Garcia-Recio, Susana, et al., "Biological and Pharmacological Aspects of the NK1-Receptor," BioMed research international, 2015 (pp. 1-15).
Zielinski, Mark R., et al., "Substance P and the neurokinin-1 receptor regulate electroencephalogram non-rapid eye movement sleep slow-wave activity locally." Neuroscience, 284, Jan. 22, 2015 (pp. 260-272).
Bend, Eric G., et al., "NALCN channelopathies: Distinguishing gain-of-function and loss-of-function mutations." Neurology, 87, 11, 2016 (pp. 1131-1139).
Funato, Hiromasa, et al., "Forward-genetics analysis of sleep in randomly mutagenized mice." Nature, 539, 7629, 2016 (pp. 378-383).
Gal, Moran, et al., "A novel homozygous splice site mutation in NALCN identified in siblings with cachexia, strabismus, severe intellectual disability, epilepsy and abnormal respiratory rhythm." European journal of medical genetics, vol. 59, Issue 4, Apr. 2016 (pp. 204-209).
Mashaghi, Alireza, et al., "Neuropeptide substance P and the immune response." Cellular and molecular life sciences, 73, 22, 2016 (pp. 4249-4264).
Severini, Cinzia, et al., "Substance P and Alzheimer's Disease: Emerging Novel Roles." Current Alzheimer Research, 13, 9, 2016 (pp. 964-972).
Johnson, M., et al., "The Therapeutic Potential of Targeting Substance P/NK-1R Interactions in Inflammatory CNS Disorders." Frontiers in cellular neuroscience, 10, Jan. 4, 2017 (pp. 1-14).
Bramswig, Nuria C., et al., "Genetic variants in components of the NALCN-UNC80-UNC79 ion channel complex cause a broad clinical phenotype (NALCN channelopathies)." Human genetics, 137, Sep. 9, 2018 (pp. 753-768).
Campbell, Jamie, et al. "NALCN Dysfunction as a Cause of Disordered Respiratory Rhythm with Central Apnea." Pediatrics, 141.Supplement 5, 2018 (pp. S485-S490).
Ford, Neil C. et al., "NALCN channels enhance the intrinsic excitability of spinal projection neurons." Pain, vol. 159, No. 9, Sep. 2018 (pp. 1719-1730).
Bouasse, Malik, et al., "Functional expression of CLIFAHDD and IHPRF pathogenic variants of the NALCN channel in neuronal cells reveals both gain-and loss-of-function properties." Scientific reports, 9, 1, Aug. 13, 2019 (pp. 1-14).

(56) References Cited

OTHER PUBLICATIONS

Hahn, Suyun, et al., "N-benzhydryl quinuclidine compounds are a potent and Src kinase-independent inhibitor of NALCN channels." *British Journal of Pharmacology*, 177, 16, May 6, 2020 (pp. 3795-3810).

* cited by examiner

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: M_NALCN_primer_F

<400> SEQUENCE: 1

```
tgatgggagc ctgtgtgatt                                               20

<210> SEQ ID NO 2
<211> LENGTH: 20
<212> TYPE: DNA
<213> ORGANISM: Artificial Sequence
<220> FEATURE:
<223> OTHER INFORMATION: M_NALCN_primer_R

<400> SEQUENCE: 2
acagtgccaa acagaaccac                                               20

<210> SEQ ID NO 3
<211> LENGTH: 20
<212> TYPE: DNA
<213> ORGANISM: Artificial Sequence
<220> FEATURE:
<223> OTHER INFORMATION: H_NALCN_primer_F

<400> SEQUENCE: 3
tcagaaactt ttgccgggta                                               20

<210> SEQ ID NO 4
<211> LENGTH: 20
<212> TYPE: DNA
<213> ORGANISM: Artificial Sequence
<220> FEATURE:
<223> OTHER INFORMATION: M_NALCN_primer_F

<400> SEQUENCE: 4
tcttcgaaac ggggactcaa                                               20
```

COMPOSITION FOR INHIBITING SODIUM LEAK CHANNEL (NALCN), COMPRISING N-BENZHYDRYL QUINUCLIDINE DERIVATIVES

GOVERNMENT INTEREST

The claimed invention was undertaken with the support of "Intrinsic and Evoked Firing Mechanisms of Midbrain Dopamine Pacemaker Neurons" Grant No. 1711067776, funded by National Research Foundation of Korea.

CROSS-REFERENCE TO RELATED APPLICATIONS

This application claims the benefit under 35 USC 119(a) of Korean Patent Application Nos. 10-2018-0080227 filed on Jul. 10, 2018, in the Korean Intellectual Property Office, the entire disclosure of which is incorporated herein by reference for all purposes.

BACKGROUND

1. Field

This application relates to a composition for inhibiting a sodium leak channel (NALCN), comprising a N-benzhydryl quinuclidine (NBQN) derivative.

2. Description of the Background

The resting membrane potential (RMP) and basal excitability of neurons are determined by dynamic balance of ions through various ion channels. Although the RMP is primarily maintained by potassium (K+) channels, the RMP of most neurons is in a range of −50 to −80 mV, which is depolarized more than the potassium equilibrium potential (EK). It suggests that background depolarizing conductances for ions of sodium and calcium are also contributing to the RMP. Among them, the sodium leak current has been regarded as a major contributor maintaining the RMP depolarized more than EK. However, for a long time, it has not been clear which type of ion channels mainly determines RMP depolarized more than EK and affects basal excitability in many cells including neurons. Very recently, molecular identity of the sodium leak channel is identified as NALCN.

Sodium leak channel (NALCN) is a Na+ permeable nonselective cation channel that allows for continuous transport of sodium ions through a cell membrane. NALCN is also called Rb21 in rats, VGCNL-1 in humans, NA in *Drosophila melanogaster*, and NCA-1/2 in *Caenorhabditis elegans*. In recent studies, it has been shown that NALCN is a tetrodotoxin (TTX)-resistant and voltage-independent nonselective cation channel which is widely expressed in many organs and tissues including the central nervous system (CNS). However, NALCN primarily conducts sodium ions under physiological conditions. The main functions of NALCN, as a sodium leak channel, are to produce inward sodium leak current, thereby contributing to determination of proper resting membrane potential and regulating excitability of neurons.

It is also known that NALCN can be regulated by several G-protein coupled receptors (GPCRs) and forms a NALCN complex called "NALCN channelosome" along with accessory proteins such as UNC80 and UNC79 as well as Src-family of tyrosine kinases (SFKs), GPCRs, and NLF-1. NALCN physically interacts with UNC80 to mobilize SFKs to the NALCN complex, and SFKs activate the NALCN complex through tyrosine phosphorylation. In mouse hippocampal neuronal cells and dopaminergic neurons located in ventral tegmental area (VTA) of the midbrain, peptide neurotransmitters such as substance P (SP) and neurotensin (NT) bind to GPCRs and activate NALCN through a G-protein-independent but SFK-dependent pathway. In addition, in pancreatic beta cells, acetylcholine (ACh) binds to muscarinic acetylcholine receptor type 3 (M3R) and activates NALCN through a G-protein-independent but SFK-dependent pathway. However, contrary to SP and NT which require UNC79, UNC80 and SFKs to activate NALCN, the M3R-mediated activation of NALCN can be achieved through physical interaction between I-II loop of NALCN and i3 loop of M3R within a cell.

NALCN is mainly expressed in the central nervous system (CNS) but also in heart, adrenal gland, thyroid gland, lymph node, and islets of Langerhans. Mutation or deletion of a NALCN gene in rats causes neonatal death due to failure of regulation of respiration, pulse, and osmotic pressure, indicating that NALCN plays an important role in the brain in vivo. As described above, as importance of NALCN in excitability of neurons and maintenance of normal physiological conditions has been clarified, many attempts have been made to conduct studies for clarifying a functional role of NALCN and a mechanism thereof. However, there is no substance that inhibits only NALCN in an independent and specific manner, which makes it difficult to conduct studies.

In a case of mice with knocked-out NALCN, all individuals died within 24 hours after birth. Thus, up to now, in order to study NALCN, a method of transfecting NALCN-cloned plasmids into non-neuronal cells, a method of knocking down NALCN using virus or siRNA, or a method of isolating and culturing cells from the brain of a mouse which was stillborn due to knocked-out NALCN, and making a comparison with normal cells is mainly used. However, these methods have a problem of causing intrinsic characteristics of cells to be lost during cell culture, or having an effect on expression of other ion channels so as to lead to incompatibility with in vivo conditions, which does not make it possible to conduct precise studies. In addition, studies conducted through genetic manipulation using knockdown technology have a problem that it is difficult to distinguish effects of remaining NALCNs from reactions caused by other ion channels. Therefore, it is required to develop a substance which can selectively and completely inhibit only NALCN in a desired cell.

Meanwhile, abnormalities including mutations in NALCN and the like have been found in diseases such as infantile neuroaxonal dystrophy (INAD), autosomal-recessive syndrome with severe hypotonia, speech impairment, cognitive delay, cervical dystonia, pancreatic cancer, non-small cell lung cancer (NSCLC), glioblastoma, bipolar disorder, schizophrenia, 13q deletion syndrome, alcoholism, restless legs syndrome, autism, Alzheimer's disease, epilepsy, type 2 diabetes, and sleep disturbance, among which many diseases are found to develop due to abnormality of NALCN. However, there have been no studies on substances capable of independently regulating NALCN, which makes it difficult to take a fundamental approach to treatment of the above-mentioned diseases.

The above information is presented as background information only to assist with an understanding of the present disclosure. No determination has been made, and no assertion is made, as to whether any of the above might be applicable as prior art with regard to the disclosure.

SUMMARY

This Summary is provided to introduce a selection of concepts in simplified form that are further described below in the Detailed Description. This Summary is not intended to identify key features or essential features of the claimed subject matter, nor is it intended to be used as an aid in determining the scope of the claimed subject matter.

In one general aspect, a composition for inhibiting a sodium leak channel includes, as an active ingredient, N-benzhydryl quinuclidine, or a N-benzhydryl quinuclidine derivative represented by the following Formula 1, wherein in the following Formula 1, R is an unsubstituted or substituted benzyl group

[Formula 1]

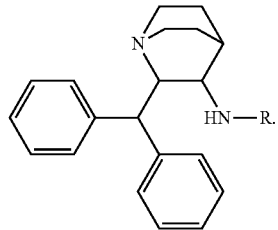

R may be

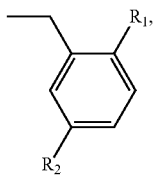

and

R1 and R2 may be, independently of each other, hydrogen, halogen, $C_{1-4}$ alkyl, $C_{1-4}$ haloalkyl, or $C_{1-4}$ alkoxy.

R1 may be hydrogen, halogen, or methoxy, and R2 may be hydrogen or $C_{1-4}$ alkyl.

the N-benzhydryl quinuclidine derivative may be 2-(diphenylmethyl)-N-(2-iodobenzyl)quinuclidin-3-amine, 2-(diphenylmethyl)-N-(2-methoxybenzyl)quinuclidin-3-amine, or (2S,3S)-2-(diphenylmethyl)-N-[2-methoxy-5-(2-methyl-2-propanyl)benzyl]quinuclidin-3-amine.

In another general aspect, a pharmaceutical composition for preventing or treating a disease resulting from abnormality of sodium leak channel, includes as an active ingredient, N-benzhydryl quinuclidine, a N-benzhydryl quinuclidine derivative represented by the above Formula 1, or a pharmaceutically acceptable salt thereof.

The disease resulting from abnormality of sodium leak channel may be one or more diseases selected from the group consisting of infantile neuroaxonal dystrophy (INAD), autosomal-recessive syndrome with severe hypotonia, speech impairment, cognitive delay, cervical dystonia, pancreatic cancer, non-small cell lung cancer, glioblastoma, bipolar disorder, schizophrenia, 13q deletion syndrome, alcoholism, restless legs syndrome, autism, Alzheimer's disease, epilepsy, type 2 diabetes, and sleep disturbance.

The disease resulting from abnormality of sodium leak channel may be one or more diseases selected from the group consisting of autosomal-recessive syndrome with severe hypotonia, speech impairment, cognitive delay, cervical dystonia, 13q deletion syndrome, alcoholism, restless legs syndrome, autism, epilepsy, and sleep disturbance.

In another general aspect, a functional health food composition for preventing or ameliorating a disease resulting from abnormality of sodium leak channel includes, as an active ingredient, N-benzhydryl quinuclidine, a N-benzhydryl quinuclidine derivative represented by the above Formula 1, or a sitologically acceptable salt thereof.

In another general aspect, a method for inhibiting a sodium leak channel includes a step of administering, to an individual, N-benzhydryl quinuclidine, or a N-benzhydryl quinuclidine derivative represented by the above Formula 1.

In another general aspect, a method for treating a disease resulting from abnormality of sodium leak channels includes a step of administering, to an individual, N-benzhydryl quinuclidine, a N-benzhydryl quinuclidine derivative represented by the above Formula 1, or a pharmaceutically acceptable salt thereof.

Other features and aspects will be apparent from the following detailed description, the drawings, and the claims.

BRIEF DESCRIPTION OF DRAWINGS

FIG. 2A illustrates a view which identifies that an inward current is not created at the time of replacing sodium with NMDG, and thus verifies that the observed inward current is due to NALCN, while identifying that PP1 has no effect on a background current but decreases a NT-induced inward current. In addition, FIGS. 2B and 2C illustrate views which show average Na+ current amplitudes caused by NT at −60 mV and which identify that intensity of a background current is decreased by L703606 and an inward current induced by NT stimulus is inhibited. FIG. 2D illustrates views which schematically represent effects of L703606 on basal current and change of current caused by NT stimulus which are identified in FIGS. 2A, 2B, and 2C.

FIG. 4A illustrates a view which identifies intensities of inward currents induced by CCh in wild-type HEK293T cells and HEK293T cells that have been transfected with M3R and NALCN. FIG. 4B illustrates a view which identifies a strong inward current induced by CCh stimulus in transfected HEK293T cells that express GFP, and inhibition thereof caused by PP1. FIG. 4C illustrates a view which identifies that NALCN activated by CCh is converted to an inactive state by L703606 and that an inward current which is insufficiently decreased by PP1 is immediately converted to a background current state due to treatment with L703606. In addition, FIG. 4D illustrates a view which identifies that CCh causes a strong inward current to be created in the presence of PP1, but even CCh stimulus has no effect on a current in the presence of L703606. FIG. 4E illustrates views which schematically represent average current intensities caused by the above CCh, PP1, and L703606, and a relationship between voltages and currents.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
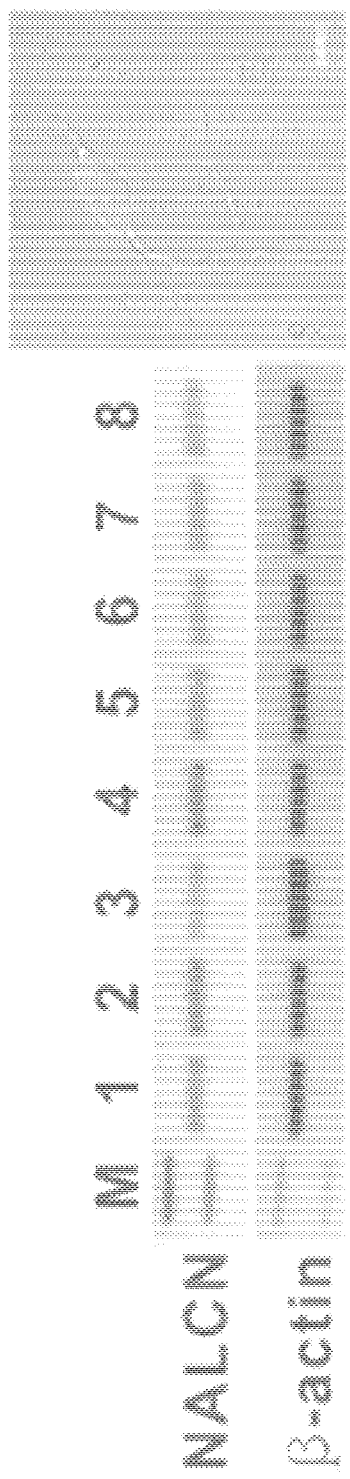
FIG. 1 illustrates a view which identifies expression of NALCN by selecting cells that express GFP among dopaminergic neurons.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after gaining an understanding of the disclosure of this application. For example, the sequences of operations described herein are merely examples, and are not limited to those set forth herein, but may be changed, as will be apparent after gaining an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have merely been provided to illustrate some of the many possible ways of implementing the methods, apparatuses, compositions, and/or systems described herein that will be apparent after an understanding of the disclosure of this application. The features of the examples described herein may be combined in various ways as will be apparent after an understanding of the disclosure of this application. Further, although the examples described herein have a variety of configurations, other configurations are possible as will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

The terminology used herein is for describing various examples only, and is not to be used to limit the disclosure. As used herein, the term "and/or" includes any one and any combination of any two or more of the associated listed items; likewise, "at least one of" includes any one and any combination of any two or more of the associated listed items. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Throughout the present specification, the phrase "combination(s) thereof" included in a Markush-type expression denotes one or more mixtures or a combination selected from the group consisting of components stated in the Markush-type expression, that is, denotes that one or more components selected from the group consisting of the components are included.

Throughout this specification, terms such as "first," "second," "A," or "B" are used to distinguish the same terms from each other. Also, the singular forms "a," "an," and "the" are intended to include the plural forms as well, unless the context clearly indicates otherwise. In this specification, a singular form is contextually interpreted as including a plural form as well as a singular form unless specially stated otherwise.

In this specification, the term "X-based" may mean that a compound includes a compound corresponding to X or a derivative of X. The term "derivative" means a compound that is derived from a specific compound as a mother compound by functional group introduction, oxidation, reduction, atom substitution, or the like, to the extent that the structure and properties of the mother compound do not change.

In this specification, B being placed on A means that B is placed in direct contact with A or placed over A with another layer interposed therebetween and thus should not be interpreted as being limited to B being placed in direct contact with A.

In this specification, the phrase "X-based repeating unit" means a repeating unit that is derived from an X-based compound obtained through polymerization in which a polymer is generated by using the X-based compound as a monomer.

In this specification, the phrase "difference between A and B" means an absolute value unless specially stated otherwise. That is, even when B is smaller than A, B minus A has the same difference as A minus B.

Due to manufacturing techniques and/or tolerances, variations of the shapes shown in the drawings may occur. Thus, the examples described herein are not limited to the specific shapes shown in the drawings, but include changes in shape that occur during manufacturing.

The use of the term "may" with respect to an example or embodiment, for example, as to what an example or embodiment may include or implement, means that at least one example or embodiment exists in which such a feature is included or implemented while all examples and embodiments are not limited thereto.

The disclosure of this application identifies NALCN-specific inhibitory activity of N-benzhydryl quinuclidine derivatives, in the examples described herein.

Accordingly, an object of the present disclosure is to provide a composition for specifically inhibiting a NALCN channel, comprising, as an active ingredient, N-benzhydryl quinuclidine or a derivative thereof, and a pharmaceutical composition for preventing or treating a disease resulting from abnormality of sodium leak channel, comprising the above composition.

The examples described herein identify that L703606 (2-(Diphenylmethyl)-N-(2-iodobenzyl)quinuclidin-3-amine), which is known as an antagonist of neurokinin-1 (NK-1) receptor, inhibits a NALCN channel regardless of the SFKs. As a result of more specific studies, the disclosure of this application identifies that NBQN compounds including L703606 not only inhibits both the background sodium leak currents and NT-evoked inward sodium currents, but also hyperpolarizes membrane potential in native conditions, and identifies that the NBQN compounds have no effect on nonselective cation channels (TRPCs) other than NALCN, as disclosed in the one or more examples described herein.

In the present disclosure, PP1 is SFK inhibitor. PP1 has four catalytic subunit isoforms, which are encoded by three different genes: PPP1α/A, PPP1β/B, and PPP1γ/C. PPP1CC1 (PP1γ1) and PPP1CC2 (PP1γ2) are the alternatively spliced variants generated from the single gene PP1γ. This catalytic subunit interacts with more than 200 types of regulatory subunits, which are known as PP1 interacting proteins (PIPs). The PIPs control PP1 activity, subcellular location, and substrate specificity. Although PP1α, PP1β, and PP1γ1 are ubiquitous, PP1γ2 is predominantly expressed in the testis and appears to be the only isoform in sperm. The PP1γ2 isoform has been detected in mouse, hamster, bull, primate, and human sperm.

In the present disclosure, PCR (Polymerase chain reaction) is a method widely used in molecular biology to make many copies of a specific DNA segment. Using PCR, a single copy (or more) of a DNA sequence is exponentially amplified to generate thousands to millions of more copies of that particular DNA segment. PCR is now a common and often indispensable technique used in medical laboratory and clinical laboratory research for a broad variety of applications including biomedical research and criminal forensics.

In the present disclosure, RT-PCR (Reverse transcription polymerase chain reaction) is a laboratory technique combining reverse transcription of RNA into DNA (in this context called complementary DNA or cDNA) and amplification of specific DNA targets using polymerase chain reaction (PCR). It is primarily used to measure the amount of a specific RNA. This is achieved by monitoring the amplification reaction using fluorescence, a technique called real-time PCR or quantitative PCR (qPCR). Combined RT-PCR and qPCR are routinely used for analysis of gene expression and quantification of viral RNA in research and clinical settings.

In the present disclosure, ZD7288 (4-(N-ethyl-N-phenylamino)-1,2-dimethyl-6-(methylamino) pyrimidinium chloride) is a selective hyperpolarization-activated cyclic nucleotide-gated (HCN) channel blocker. ZD7288 has been widely used as a tool in the study of hyperpolarization-activated cyclic nucleotide-gated channels (HCN channels), and to test the relationships between HCN channels and heart and brain function.

In the present disclosure, SKF96365 is receptor-operated calcium channel blocker. SKF96365 (SKF) was originally described as a selective blocker of receptor-mediated Ca entry (RMCE) over Ca release from internal stores in non-excitable cells such as platelets, endothelial cells and neutrophils. In the interim, SKF has been used extensively to elucidate the contributions of RMCE or store-operated Ca entry (SOCE) in many physiological processes. Transient receptor potential canonical type (TRPC) channels have been demonstrated to mediate RMCE and in some cases SOCE (alternatively known as capacitative Ca entry), and are thought to be a major molecular target underlying inhibition by SKF.

The present inventors have, as disclosed in the examples described herein, identified that N-benzhydryl quinuclidine and derivatives thereof have an effect of specifically inhibiting NALCN channels.

The N-benzhydryl quinuclidine (NBQN) of the examples described herein has a structure in which a nitrogen atom and a benzhydryl functional group are bound to a quinuclidine skeleton. The NBQN and NBQN derivatives represented by the following Formula 1, of the examples described herein, may be produced by methods described in U.S. Patent Application Publication No. 2009/0099364.

[Formula 1]

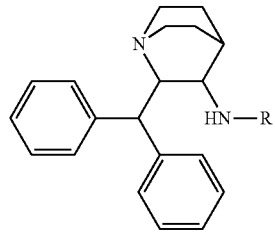

In the formula, R may be a substituted or unsubstituted benzyl group, and in a case where R is

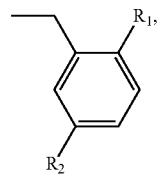

R1 and R2 may be, independently of each other, hydrogen, halogen, $C_{1-4}$ alkyl, $C_{1-4}$ haloalkyl, or $C_{1-4}$ alkoxy. For example, R1 may be hydrogen, halogen, or methoxy, and R2 may be hydrogen or $C_{1-4}$ alkyl.

As the NBQN derivatives in the examples described herein, 2-(diphenylmethyl)-N-(2-iodobenzyl)quinuclidin-3-amine (Sigma-Aldrich, L703606), 2-(diphenylmethyl)-N-(2-methoxybenzyl)quinuclidin-3-amine (Tocris, CP96345), and (2S,3S)-2-(diphenylmethyl)-N-[2-methoxy-5-(2-methyl-2-propanyl)benzyl]quinuclidin-3-amine were purchased (Toronto Research Chemicals, Maropitant), and used in experiments. In the examples described herein it is identified that all of L703606, CP96345, and maropitant, which have NBQN as a mother skeleton and each of which has a different substituent, selectively inhibit NALCN. Thus, it is herein disclosed that NBQN compounds play a key role in inhibiting NALCN.

In the present disclosure, "inhibition" of NALCN includes a meaning of decreasing leak of sodium ions caused by NALCN, and also includes meanings of not only inhibiting activation of NALCN by chemical or physical stimulus but also converting NALCN, which has been activated by the stimulus, to an inactive state in an immediate or gradual manner.

Meanwhile, the purchased NBQN derivatives are known to be selective antagonists of neurokinin-1 (NK-1) receptor. However, the examples described herein disclose the discovery by the present inventors that these derivatives can be used as specific and exclusive inhibitors against NALCN.

The NK-1 receptor is expressed, as a G protein coupled receptor (GPCR), in central nervous system (CNS) and peripheral nervous system (PNS) cells, and is activated by substance P (SP) which is a neurotransmitter. The NK-1 receptor is located upstream of a signaling pathway and induces cell migration, proliferation, and antiapoptotic effects through a number of downstream signaling pathways, while functioning to transmit various stimuli such as pain, smooth muscle contraction, and inflammation.

Accordingly, NK-1 receptor antagonists have been developed to block transmission of various stimuli by the NK-1 receptor and are used to inhibit activity of the NK-1 receptor so as to treat diseases or mitigate symptoms. However, the NK-1 receptor has a myriad of downstream signaling pathways. Thus, besides disease symptoms to be blocked, an individual is subjected to various effects, and this is problematic in view of that side effects are included in the various effects. Furthermore, blockade of signaling of SP does not induce inhibition of NALCN.

Meanwhile, the sodium leak channel (NALCN) is a Na+ permeable nonselective cation channel that allows for continuous transport of sodium ions through a membrane. NALCN is also called Rb21 in rats, VGCNL-1 in humans, NA in *Drosophila melanogaster*, and NCA-1/2 in *Caenorhabditis elegans*. NALCN causes extracellular sodium ions to leak into a cell so that cell excitability is affected. Therefore, selective inhibition of NALCN blocks flow of sodium ions that leak into the cell and induces a hyperpolarization state, so that cell excitability can be regulated.

The NBQN or derivatives thereof, in the examples described herein, target NALCN among ion channels of a cell membrane, and inhibit activity thereof. Therefore, it is possible to regulate cell excitability in a more direct manner, and outcome of action thereof is predictable in that only the cell excitability is regulated and there is no downstream signaling pathway.

In examples described herein of the present disclosure, a phenomenon is observed that that L703606 inhibits NALCN activation caused by a neurotransmitter in dopaminergic neurons and HEK293T cells that have been transfected with M3R and NALCN, to identify that L703606 rapidly returns an inward current, which has been increased by the neurotransmitter, to a state before stimulus, and to identify that a current induced by NALCN is voltage-independent and is blocked by L703606 (see Examples 1 and 2).

In addition, in examples described herein, in order to identify whether the NBQN derivatives have specific and exclusive inhibitory activity against NALCN, the present disclosure identifies effects of L703606 on an inward current using HEK293T cells, that have been transfected with M3R and a TRPC channel, under a condition where sodium and potassium are removed, cesium is added, and calcium and magnesium concentrations are normal. As a result, it was identified that L703606 has no effect on change of inward current in the HEK293T cells that have been transfected with the TRPC channel. Thus, it can be seen that the NBQN derivatives exhibit specific and exclusive inhibitory activity against only NALCN among cell membrane ion channels (See Example 3).

In addition, in examples of the present disclosure, in order to identify whether a NK-1 receptor inhibitor simultaneously inhibits NALCN and which is a key skeleton for inhibition of NALCN in L703606, the present disclosure uses CP96345, maropitant, CP99994, and L733060, and effects of the respective compounds on flow of ions caused by NALCN is observed in the same manner as described above. As a result, it has been identified that CP99994 and L733060 inhibit the NK-1 receptor but has no effect on a current induced by NALCN, and that CP96345 and maropitant which have NBQN as a common central structure inhibits NALCN similarly to L703606 (see Example 4).

From the above, it can be seen that the NBQN and derivatives thereof, of the present disclosure, selectively inhibit NALCN. The NBQN or derivatives thereof inhibit NALCN activity of a cell membrane, and thus can be used for the prevention, treatment, or amelioration of a disease resulting from abnormality of NALCN.

In the present disclosure, a "disease resulting from abnormality of NALCN" is not limited as long as the disease is caused by abnormality of NALCN in neuronal cells, and includes degenerative cranial nerve diseases and excitatory cranial nerve diseases. In addition, the disease includes diseases which are not caused by abnormal action of NALCN but can be prevented or treated by inhibiting activity of NALCN. Non-limiting examples of the disease resulting from abnormality of NALCN include infantile neuroaxonal dystrophy (INAD), autosomal-recessive syndrome with severe hypotonia, speech impairment, cognitive delay, cervical dystonia, pancreatic cancer, non-small cell lung cancer (NSCLC), glioblastoma, bipolar disorder, schizophrenia, 13q deletion syndrome, alcoholism, restless legs syndrome, autism, Alzheimer's disease, epilepsy, type 2 diabetes, and sleep disturbance.

For example, among the diseases resulting from abnormality of NALCN, diseases such as autosomal-recessive syndrome with severe hypotonia, speech impairment, cognitive delay, cervical dystonia, 13q deletion syndrome, alcoholism, restless legs syndrome, autism, epilepsy, and sleep disturbance are diseases that develop due to only abnormality of NALCN irrespective of other neurotransmitters, and can be prevented, treated, or ameliorated in a more fundamental manner by applying the NBQN derivatives of the examples described herein.

Accordingly, the present disclosure is capable of providing a method for preventing or treating a disease resulting from abnormality of NALCN by administering NBQN or a derivative thereof to an individual. In the present disclosure, an "individual" is not limited as long as the individual is a mammal such as a rat, a mouse, a domestic animal, and a human. For example, the individual may be a human.

In addition, the present disclosure provides a use of N-benzhydryl quinuclidine, a N-benzhydryl quinuclidine derivative represented by the above Formula 1, or a pharmaceutically acceptable salt thereof, for the production of a medicament for preventing or treating a disease resulting from abnormality of NALCN channels.

In the present disclosure, "prevention" means all actions that allow various diseases caused by NALCN to be delayed by inhibition of activity or inactivation of NALCN which is caused by administration of a composition according to the examples described herein. "Treatment" means all actions that allow symptoms of various diseases caused by NALCN to be improved or advantageously altered by administration of a pharmaceutical composition according to the present disclosure. "Amelioration" means all actions that allow various parameters, such as a degree of symptoms, associated with various diseases caused by NALCN to be alleviated by administration of a composition according to the examples described herein.

In the present disclosure, the pharmaceutical composition may further comprise suitable carriers, excipients, and diluents which are commonly used in the production of pharmaceutical compositions.

In the present disclosure, a "carrier", which is also referred to as a vehicle, refers to a compound that facilitates addition of a protein or peptide into cells or tissues. For example, dimethylsulfoxide (DMSO) is a commonly used carrier that facilitates introduction of many organic substances into cells or tissues.

In the present disclosure, a "diluent" is defined as a compound which not only stabilizes a biologically active form of a protein or peptide of interest but also is diluted in water in which the protein or peptide is dissolved. Salts dissolved in buffer solutions are used as diluents in the art. A commonly used buffer solution is phosphate buffered saline, since the phosphate buffered saline mimics a salt condition in human solution. Since buffer salts can control a pH of a solution at low concentrations, buffer diluents rarely modify biological activity of compounds. The NBQN or derivatives thereof used herein may be administered, to a human patient, either as such, or as a pharmaceutical composition which is mixed with other ingredients, such as in combination therapy, or with an appropriate carrier or excipient.

In addition, the pharmaceutical composition for preventing or treating a disease resulting from abnormality of NALCN, comprising, as an active ingredient, NBQN or a derivative thereof according to the examples described herein can be formulated in the form of external formulations, such as powders, granules, tablets, capsules, suspensions, emulsions, syrups, and aerosols, and sterile injection solutions, according to the respective conventional methods, and used. Examples of carriers, excipients, and diluents which can be contained in the composition include lactose, dextrose, sucrose, oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, and combinations thereof. In a case of being made into formulations, the formulations are prepared by using commonly used diluents or excipients such as fillers, extenders, binders, wetting agents, disintegrants, and surfactants. Solid formulations for oral administration include tablets, pills, powders, granules, capsules, and the like. Such solid formulations are prepared by mixing the above compound with at least one excipient, for example, starch, calcium carbonate, sucrose or lactose, gelatin, and the like. In addition, besides simple excipients, lubricants such as magnesium stearate and talc may also be used. Liquid formulations for oral administration include suspensions, solutions, emulsions, syrups, and the like. The liquid formulations can contain various excipients such as wetting agents, sweetening agents, fragrances, and preservatives, in addition to water and liquid paraffin which are commonly used simple diluents. For example, formulations for parenteral administration include sterile aqueous solutions, non-aqueous solutions, suspensions, emulsions, freeze-dried formulations, and suppositories. For the non-aqueous solutions and the suspensions, propylene glycol, polyethylene glycol, vegetable oil such as olive oil, injectable ester such as ethyl oleate, and the like, and combinations thereof can be used. As example bases for the suppositories, Witepsol, macrogol, Tween 61, cacao fat, laurin fat, glycerogelatin, and the like, and combinations thereof can be used.

Besides, the examples described herein provide a food composition comprising, as an active ingredient, NBQN or a derivative thereof. In addition, NBQN or a derivative thereof may be added to food for the purpose of ameliorating a disease resulting from abnormality of NALCN. In the examples described herein, the food includes functional food and functional health food. In a case where NBQN or a derivative thereof, of the examples described herein, is used as a food additive, the NBQN or a derivative thereof may be added as it is or may be used together with other foods or food ingredients, and may be suitably used according to a conventional method. An amount of the active ingredient to be mixed may be suitably determined depending on an intended use (prevention, health or therapeutic treatment). Generally, in the production of a food or beverage, LGI3 or a LGI3-derived peptide, of the examples described herein, is added in an amount of equal to or less than 15% by weight, for example, equal to or less than 10% by weight, with respect to raw materials. However, in a case of long-term intake for health and hygiene purposes or for health control purposes, the amount may be equal to or less than the above range. The active ingredient may be used in an amount of equal to or greater than the above range, since there is no problem in terms of safety.

There is no particular limitation on a type of the food. Examples of the food to which the above substance can be added include meats, sausages, bread, chocolates, candies, snacks, confections, pizza, ramen, other noodles, gums, dairy products including ice cream, various soups, beverages, tea, drinks, alcoholic beverages, vitamin complexes, and the like, and combinations thereof. All functional health foods in a conventional sense are included.

A health beverage composition according to the examples described herein may contain various flavoring agents or natural carbohydrates, or the like as additional ingredients similarly to conventional beverages. The above-mentioned natural carbohydrates are a monosaccharide such as glucose and fructose, a disaccharide such as maltose and sucrose, a polysaccharide such as dextrin and cyclodextrin, and sugar alcohol such as xylitol, sorbitol, and erythritol. As the flavoring agent, a natural flavoring agent such as thaumatin and a stevia extract, a synthetic flavoring agent such as saccharin and aspartame, or the like may be used. A proportion of the natural carbohydrates may be generally about 0.01 to 0.20 g, for example, about 0.04 to 0.10 g, per 100 mL of the composition of the examples described herein.

In addition to the above, the composition of the examples described herein may further contain various nutrients, vitamins, electrolytes, flavors, colorants, pectic acid and salts thereof, alginic acid and salts thereof, organic acids, protective colloid thickeners, pH adjusting agents, stabilizers, preservatives, glycerin, alcohol, carbonating agent used in carbonated beverages, and the like, and combinations thereof. Besides, the composition of the examples described herein may contain flesh for the production of natural fruit juices, fruit juice beverages, and vegetable beverages. These ingredients may be used independently or in combination. Although a proportion of these additives is not very critical, the additives are generally selected in a range of 0.01 to 0.20 parts by weight per 100 parts by weight of the composition of the examples described herein.

In addition, in the examples described herein, NBQN or a derivative thereof may be respectively used in the form of a pharmaceutically or sitologically acceptable salt thereof. As an example of the salt, an acid addition salt formed by a pharmaceutically or sitologically acceptable free acid is useful.

As used herein, for the term "salt", an acid addition salt formed by a pharmaceutically or sitologically acceptable free acid is useful. For example, the acid addition salt is obtained from inorganic acids such as hydrochloric acid, nitric acid, phosphoric acid, sulfuric acid, hydrobromic acid, hydroiodic acid, nitrous acid, or phosphorous acid, and non-toxic organic acids such as aliphatic mono- and dicarboxylates, phenyl-substituted alkanoates, hydroxyalkanoates and alkanedioates, aromatic acids, and aliphatic and aromatic sulfonic acids. Such pharmaceutically or sitologically non-toxic salts include, for example, sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluene sulfonate, chlorobenzene sulfonate, xylene sulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, or mandelate.

The acid addition salt according to the examples described herein may be produced by a conventional method, for example, by dissolving NBQN or a derivative thereof in an excess amount of an acid aqueous solution to form a salt and precipitating the salt using a water-miscible organic solvent such as methanol, ethanol, acetone, and acetonitrile. In addition, the acid addition salt may be produced by evaporating the solvent or excess acid in the mixture and then performing drying, or by performing suction filtration of the precipitated salt.

In addition, a base may be used to form a pharmaceutically or sitologically acceptable metal salt. An alkali metal or alkaline earth metal salt is obtained, for example, by dissolving the compound in an excess amount of an alkali metal hydroxide or alkaline earth metal hydroxide solution, filtering a compound salt which is not dissolved, and evaporating and drying the filtrate. At this time, as a metal salt, it is pharmaceutically suitable to produce a sodium, potassium, or calcium salt. A silver salt that corresponds thereto is obtained by reacting the alkali metal or alkaline earth metal salt with an appropriate silver salt (such as silver nitrate).

In addition, the NBQN or derivatives thereof, of the present disclosure, include not only pharmaceutically or sitologically acceptable salts, but also all salts, isomers, hydrates, and solvates which can be produced by conventional methods.

Hereinafter, in order to facilitate understanding of the present disclosure, specific examples will be presented. However, the following examples are provided merely for the purpose of easier understanding of the present disclosure, and the present disclosure is not limited by the following examples.

Experimental Method

1. Isolation of Midbrain Dopaminergic Neurons

In order to obtain midbrain dopaminergic neurons from mice, substantia nigra pars compacta within mouse midbrain in which GFP was expressed due to tyrosine hydroxylase (TH) promoter was cut into sections. In order to isolate tissue, the sections were subjected to treatment with a highly-concentrated glucose solution at 36.5° C. which contains papain (4 U ml-1) for 20 minutes or longer. The enzymatically-treated sections of substantia nigra pars compacta were washed with a highly-concentrated glucose solution, and then slowly agitated using Pasteur pipettes with various size holes so that the respective dopaminergic neurons were isolated. All animal experiments were conducted under approval of the Institutional Animal Care and Use Committee (IACUC) of Sungkyunkwan University School of Medicine.

2. Culture of Human Embryonic Kidney-Derived (HEK293T) Cells and Production of Transfected HEK293T Cells HEK293T cells were cultured in a DMEM (Eagle's minimal essential medium) medium containing 10% FBS and 1% antibiotics using an incubator having a condition of 37° C. and 5% $CO_2$. NALCN and TRPC cDNAs were respectively constructed using a vector that expresses GFP under an independent promoter. Lipofectamine 2000, which is used as a transfection reagent, was mixed with each plasmid and the cells were treated with the mixture. Then, after 48 hours, expression was identified. In order to identify whether normal transfection with each plasmid occurred, only the cells in which GFP was expressed were selected.

The HEK293T cells were transfected with combinations of M3R and NALCN, M3R and GFP, and M3R and TRPCs.

3. Identification of Expression of NALCN mRNA Using RT-PCR

In order to identify presence of NALCN in dopaminergic neurons, amplification was performed by PCR using mouse NALCN primers, and then loaded on agarose gel to identify expression at a size of 229 bp.

On the other hand, in order to identify presence of NALCN in transfected HEK293T cells, amplification was performed by PCR using human NALCN primers, and then loaded on agarose gel to identify expression at a size of 197 bp.

In addition, in order to identify change of NALCN expression in HEK293T cells that had been transfected to overexpress NALCN, amplification was performed by PCR using mouse NALCN primers, and then loaded on agarose gel to identify expression at a size of 178 bp.

Each PCR was carried out under a condition of 45 cycles with denaturation at 94° C. for 30 seconds, annealing at 55° C. for 30 seconds, and extension at 72° C. for 30 seconds, and sequence information for the primers is shown in Table 1 below.

TABLE 1

| Mouse NALCN primers | Forward [SEQ ID NO: 1] | 5'-TGATGGGAGCCTGTGTGATT-3' |
|---|---|---|
| | Reverse [SEQ ID NO: 2] | 5'-ACAGTGCCAAACAGAACCAC-3' |
| Human NALCN primers | Forward [SEQ ID NO: 3] | 5'-TCAGAAACTTTTGCCGGGTA-3' |
| | Reverse [SEQ ID NO: 4] | 5'-TCTTCGAAACGGGGACTCAA-3' |

4. Identification of Expression of NALCN Using Western Blot

In order to identify change of NALCN protein expression in HEK293T cells that had been transfected to overexpress NALCN, the transfected HEK293T cells were lysed in a lysis solution (phosphate-buffered saline (PBS) solution that contains 1 mM sodium orthovanadate, 1 mM sodium fluoride, complete protease inhibitor cocktail (ROCHE), and 1% Triton X-100) for 30 minutes, and then proteins were acquired. The proteins were separated by SDS-PAGE and transferred to a hydrophobic polyvinylidene difluoride (PVDF) membrane. Blocking was performed by treating the PVDF membrane with 5% skim milk, which had been dissolved in Tween Tris-buffered saline (TTBS), for 1 hour. Then, treatment with primary antibodies for NALCN, which had been diluted 1:1000, was performed at 4° C. for 18 hours. After performing washing three times, treatment with HRP-conjugated secondary antibodies was additionally performed at room temperature for 2 hours.

5. Patch-Clamp Method

Among the dopaminergic neurons isolated in Experimental Method 1, dopaminergic neurons expressing GFP were selected, and a patch pipette formed of thin glass tube was inserted into a membrane surface. After setting −60 mV as a holding potential, a current was measured. A background current was identified under the holding voltage. After treatment with NT, a current was identified. Then, additionally, an extracellular solution was treated with 10 µM of L703606, and change of current was identified. In addition, the above procedure was repeated by replacing sodium ion with N-methyl-D-glucamine (NMDG). After treating the extracellular solution with 0.5 µM of tetrodotoxin (TTX) and 30 µM of ZD7288 which are a voltage-gated sodium channel inhibitor and an HCN channel inhibitor, respectively, a voltage was measured. Additionally, change of voltage at the time of treatment with 10 µM of L703606 was identified. All data were presented as mean±standard deviation calculated at the time of treatment with the inhibitors and replacement of sodium ion, relative to a control. (* $P<0.05$,  $P<0.01$, * $P<0.001$).

Among the transfected HEK293T cells acquired in Experimental Method 2, cells expressing GFP were selected, and a patch pipette formed of a thin glass tube was inserted into a membrane surface. After setting −80 mV as a holding potential, a current was measured. Under the holding potential, treatment with carbachol (CCh) which is an activator of M3R was performed to identify a current induced by NALCN. An extracellular solution was treated with 50 µM of L703606, and change of current caused by CCh was identified. In addition, based on voltage-independent characteristics of NALCN, currents obtained by varying the voltage from −80 mV to +10 mV were measured, and change of current caused by the treatment with L703606 was recorded. All data were presented as mean±standard deviation calculated after treatment with an inhibitor relative to a control (** $P<0.01$).

Experiment Results

Figure 2A:
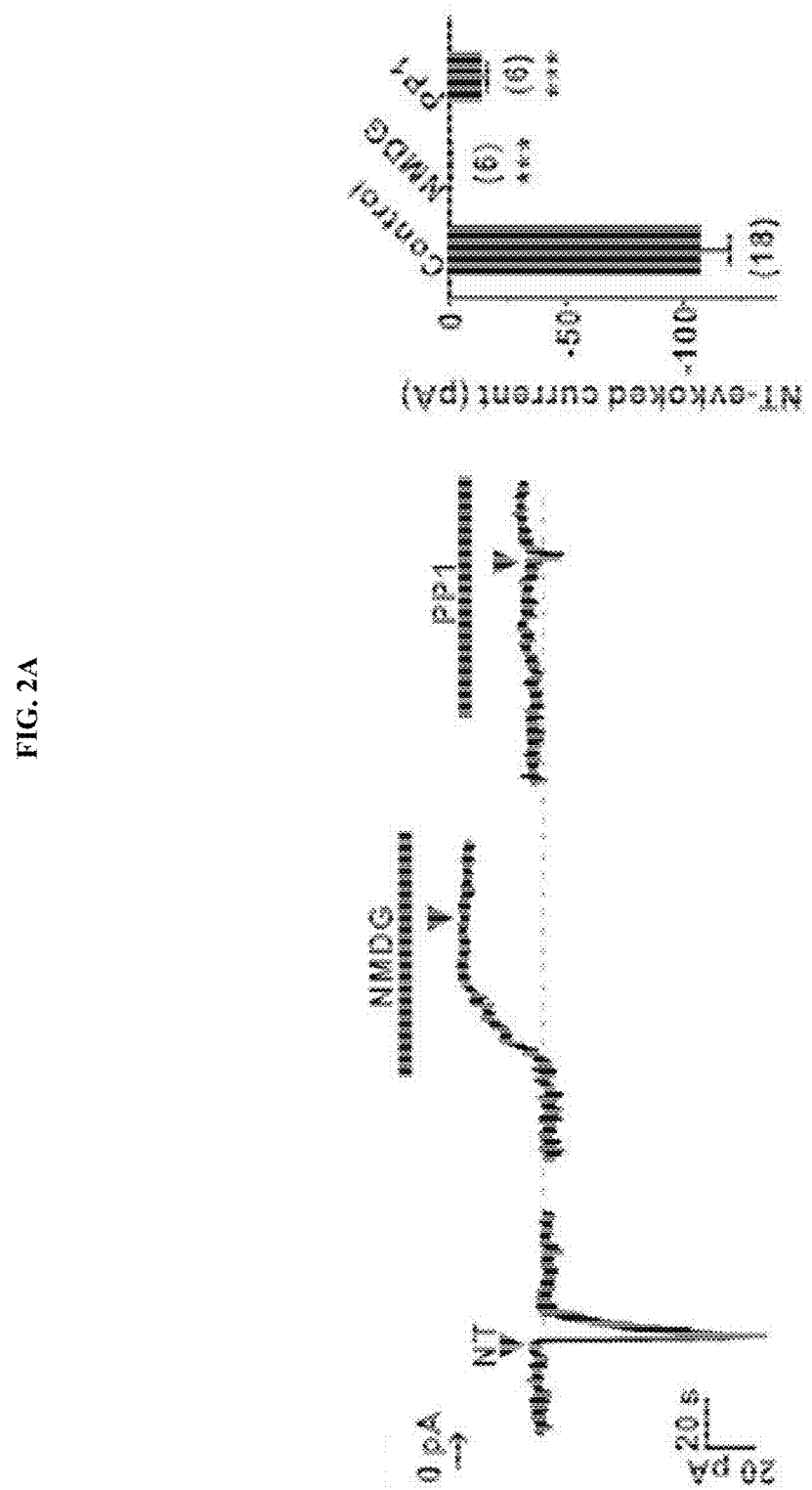
FIGS. 2A, 2B, 2C, and 2D illustrate views which identify that activity of NALCN in dopaminergic neurons is inhibited by a NBQN derivative.

Example 1. Identification of Inhibitory Effect of NBQN Derivatives on NALCN in Dopaminergic Neurons As can be identified from the RT-PCR results shown in FIG. 1, it was possible to identify that NALCN mRNA is expressed in dopaminergic neurons of midbrain, and as shown in FIG. 2A, according to patch clamping, −30 to −40 pA of the background current was created under the holding potential of −60 mV and a strong and fast inward current was induced by 1-second treatment with NT. In addition, it was possible to identify that at the time of replacing sodium with NMDG, the background current was close to 0 pA, and an inward current was not induced by the treatment with NT. From this, it can be seen that the background current is generated by sodium ions. Besides, in a case of being treated with 20 µM of PP1 which is a SFK inhibitor, it was possible to identify that there is little effect on the background current and an inward current induced by NT stimulus is remarkably decreased.

Figure 2B:
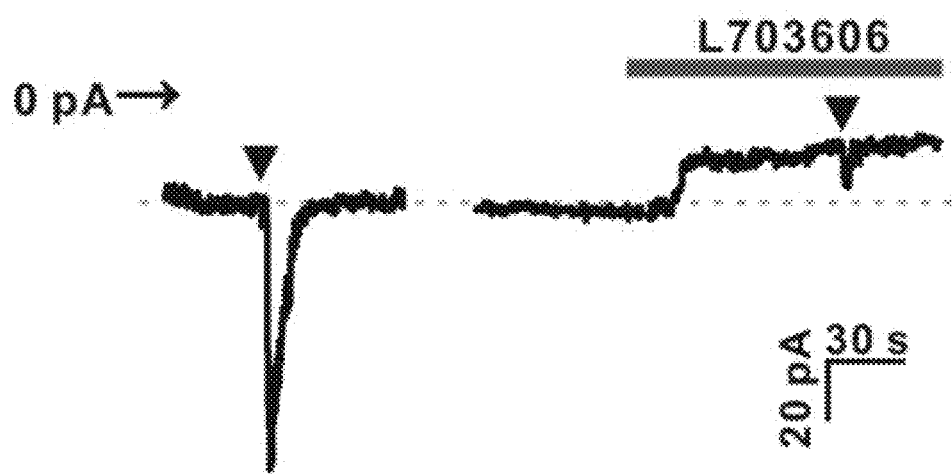
Figure 2C:
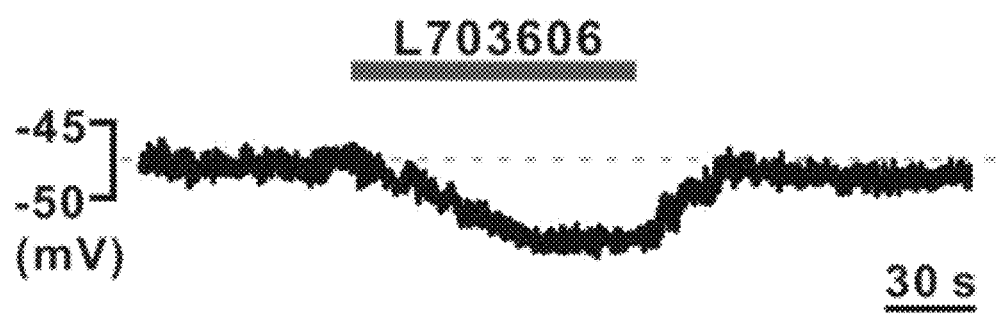
Figure 2D:
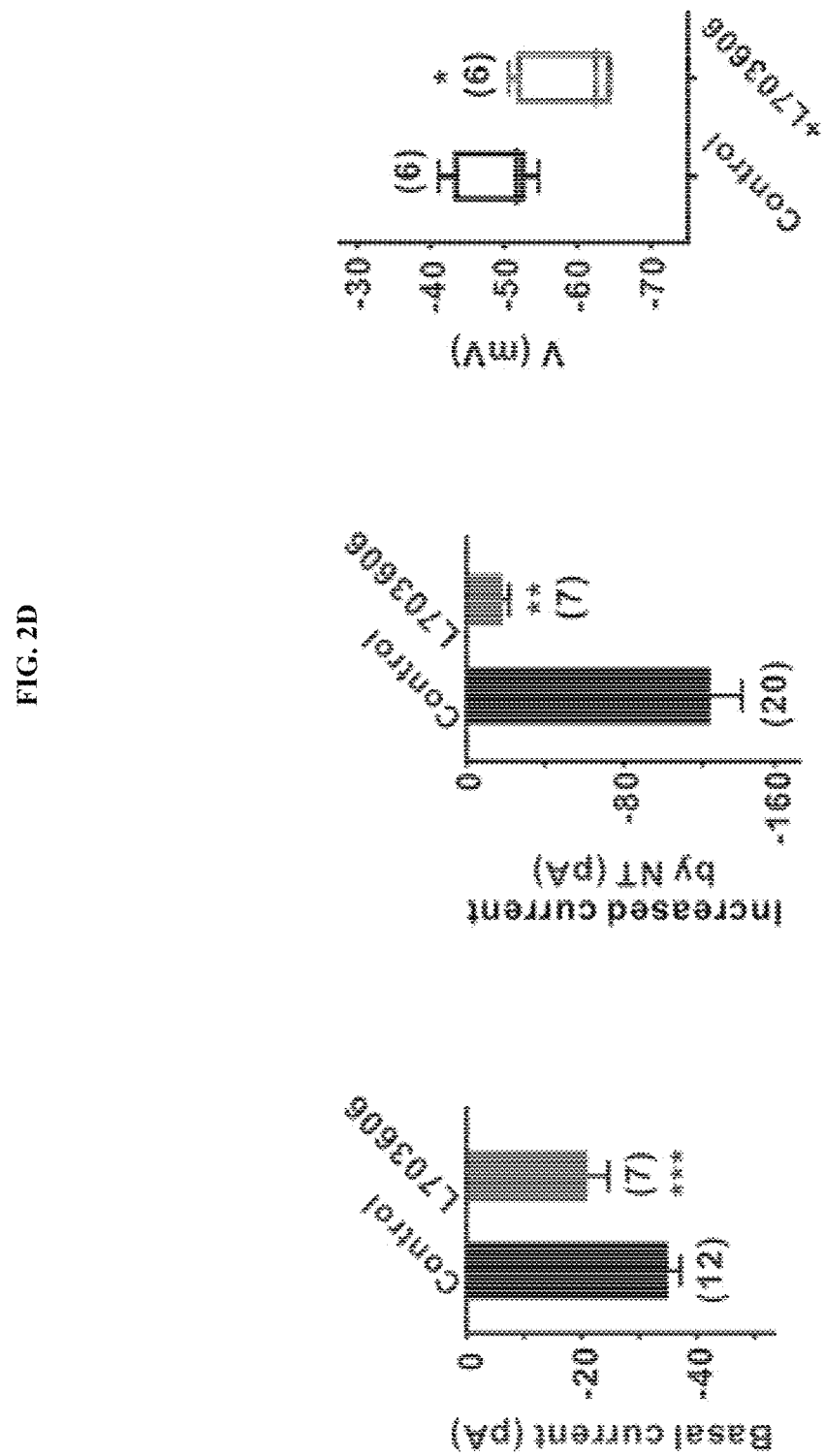

On the other hand, at the time of treatment with L703606, as shown in FIG. 2B, it was identified that the background current was decreased and a strong inward current was not induced even at the time of treatment with NT. In addition, as shown in FIG. 2C, L703606 not only completely inhibited a spontaneous activity voltage, but also induced hyperpolarization of membrane potential even under a condition where the spontaneous activity voltage was stopped by TTX and ZD7288. Changes in background current, current amplitudes induced by NT, and voltage at the time of the treatment with L703606 are graphically illustrated in FIG. 2D.

Example 2. Identification of Inhibitory Effect of NBQN Derivatives on NALCN in Transfected HEK293T Cells HEK293T cells are non-neuronal cells commonly used for transfection of genes. Based on the report that a NALCN channel is activated by M3R in pancreatic beta cells MIN6 and HEK293 cells, M3R and NALCN plasmids that had been cloned from rat brain were co-transfected into HEK293T cells to identify whether L703606 inhibits a NALCN current activated by M3R.

Figure 3:
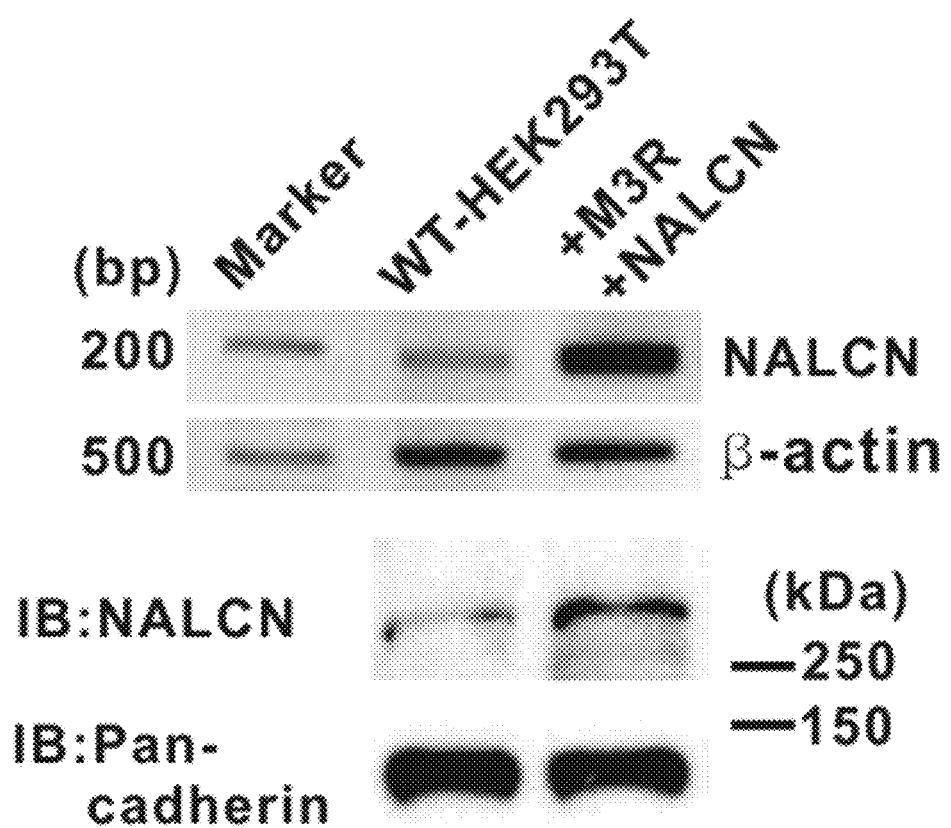
FIG. 3 illustrates a view which identifies NALCN expression levels in wild-type HEK293T cells and HEK293T cells that have been transfected with M3R and NALCN.
Figure 4A:
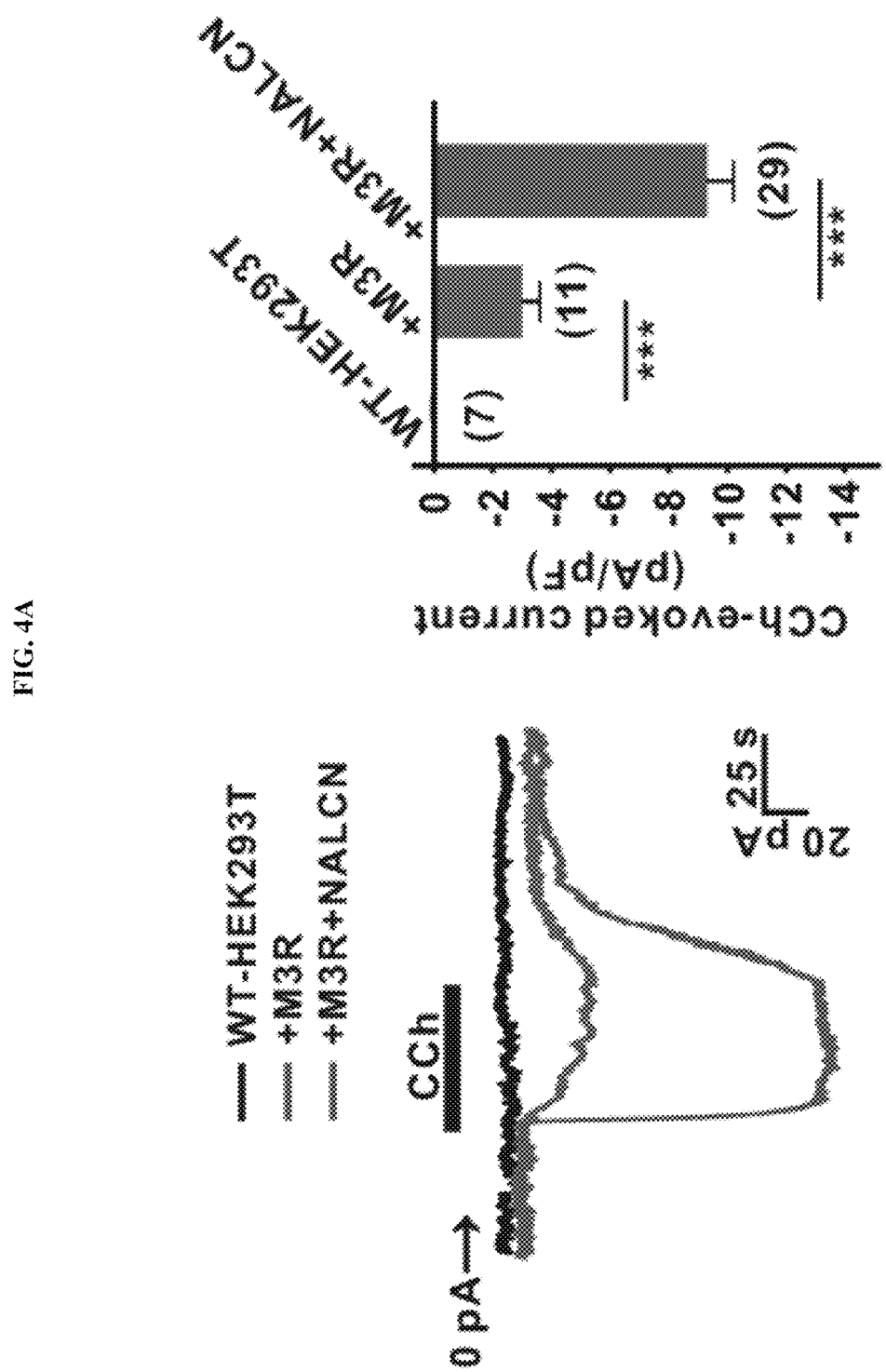
FIGS. 4A, 4B, 4C, 4D, and 4E illustrate views which identify that L703606 inhibits activation of NALCN caused by CCh in HEK293T cells that have been transfected with M3R and NALCN.

More specifically, as can be identified from the RT-PCR results shown in FIG. 3, it was possible to identify that the transfected HEK293T cells exhibit remarkably increased mRNA and protein expression levels of NALCN as compared with wild-type cells. In addition, as shown in FIG. 4A, according to patch clamping, it was possible to identify that a CCh-induced inward current was stronger than that of wild-type cells, together with increased NALCN expression.

Figure 4B:
Figure 4C:
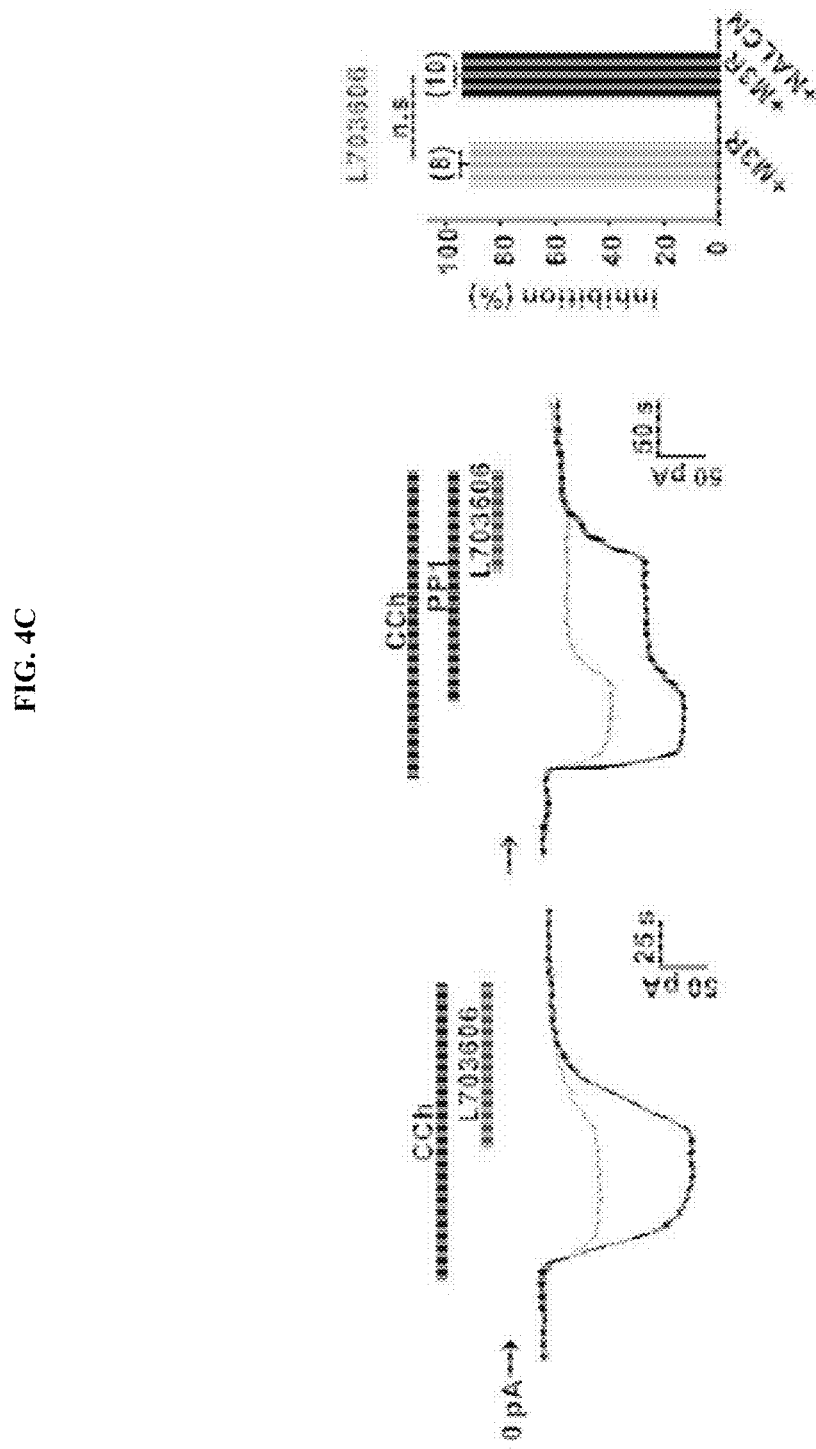

On the other hand, as shown in FIGS. 4B and 4C, treatment with PP1 decreased a magnitude of the CCh-induced inward current; however, such treatment did not greatly inhibit the CCh-induced inward current in cells that co-express M3R-NALCN, but inhibited the CCh-induced inward current by equal to or greater than 90% in cells that express M3R, which made it possible to identify that an inhibition rate of inward current obtained by PP1 is higher in the cells that express M3R than in the cells that co-express M3R-NALCN. In contrast, it was possible to identify that L703606 rapidly inhibits the CCh-induced inward current by equal to or greater than 90% in both the cells that co-express M3R-NALCN and the cells that express M3R.

Figure 4D:
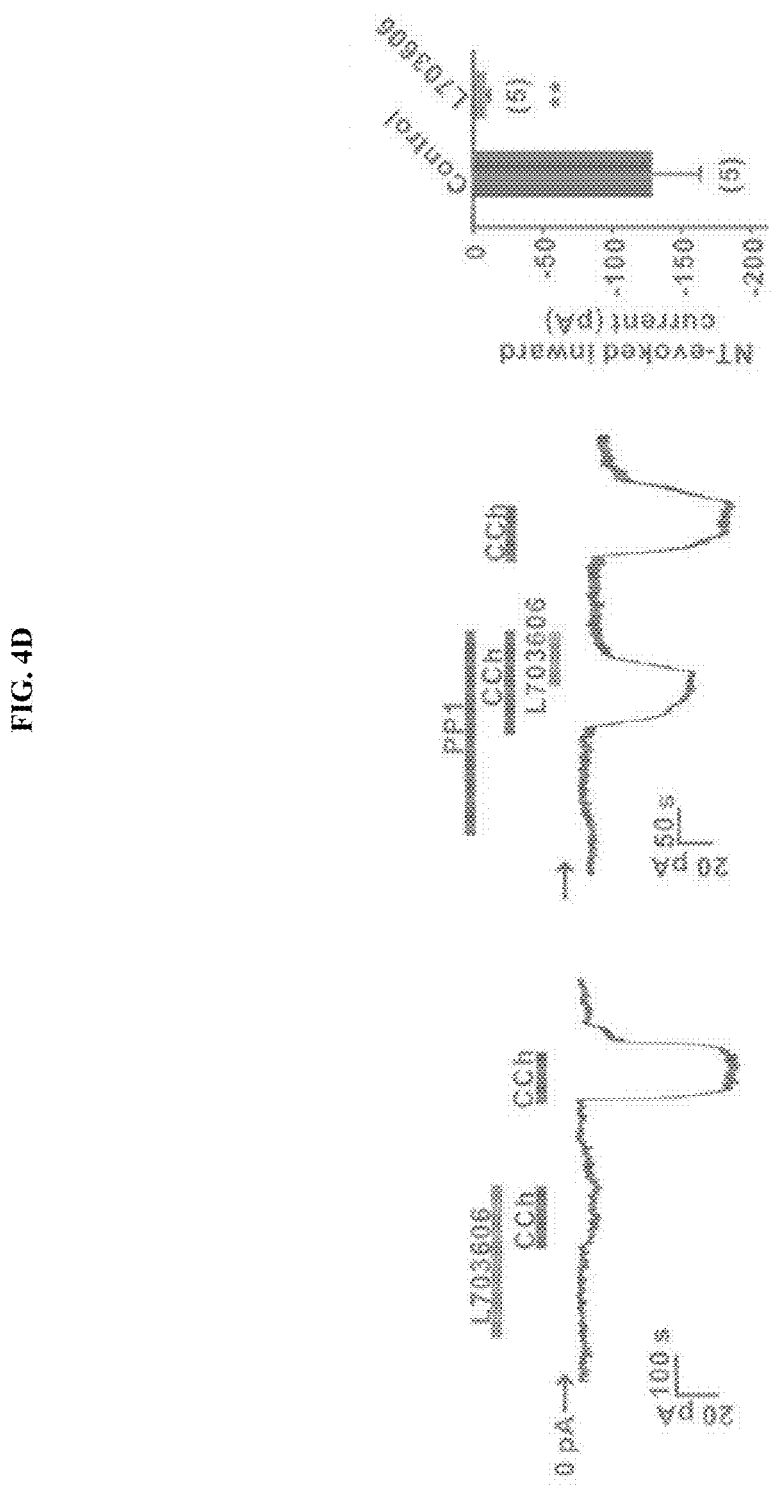

In addition, as shown in FIG. 4D, in a case where treatment with CCh is performed in the presence of L703606, it was not possible to observe activation of NALCN caused by M3R. On the other hand, in a case where treatment with CCh is performed in the presence of PP1, it was possible to identify a strong inward current induced by activation of NALCN. However, it was possible to identify a pattern of returning to the background current again immediately after treatment with L703606. Thus, it can be seen that L703606 is capable of not only inhibiting activation of NALCN, but also immediately converting the activated NALCN to an inactive state.

Figure 4E:
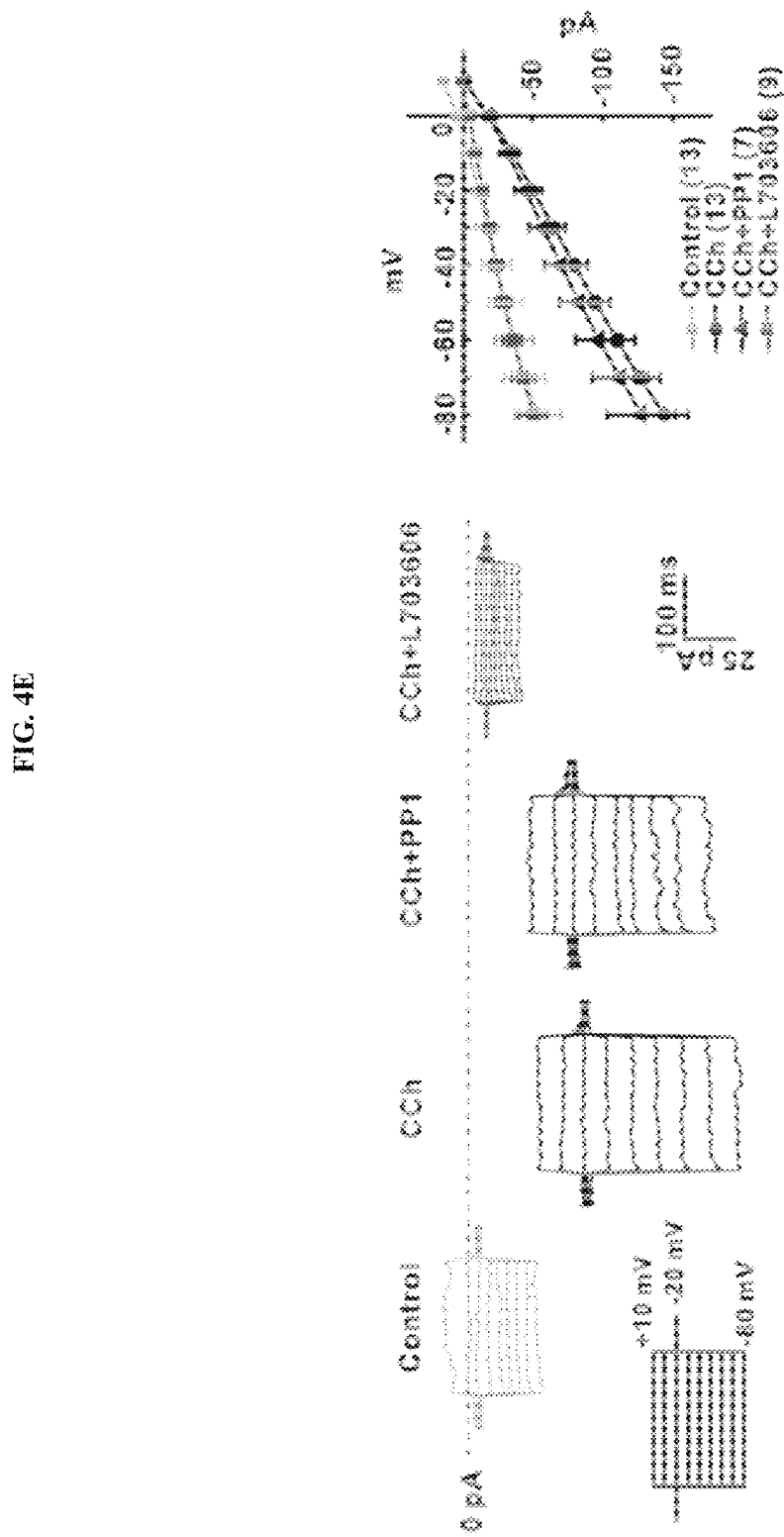

On the other hand, as shown in FIG. 4E, in a case where a voltage is changed, a CCh-induced NALCN current showed voltage-independent characteristics, and the current was decreased to a control level by L703606.

Example 3. Identification of NALCN-Specific Inhibitory Activity of NBQN Derivatives From the above, it was possible to identify NALCN inhibitory effects of the NBQN derivatives. Furthermore, in the present example, it was intended to identify whether the NBQN derivatives have specific and exclusive inhibitory activity against NALCN. Accordingly, HEK293T cells were transfected with M3R, and a transient receptor potential canonical (TRPC) 3, 4, 5, 6, or 7 channel, respectively, and the cells were immersed in a solution having a condition where sodium and potassium are removed, cesium is added, and calcium and magnesium concentrations are normal, to block all of voltage-dependent potassium ion channels, so that it was intended to effectively measure flow of charges through a TRPC channel having high permeability to calcium. The cells immersed in the solution were treated with CCh to identify a TRPC current activated by M3R and an inhibitory effect caused by L703606. On the other hand, unlike NALCN, the TRPC currents have a feature that inward currents were decreased gradually as CCh stimulus continues. Thus, comparison was made for effects of the inhibitors on an inward current induced by a second CCh stimulus.

Figure 5A:
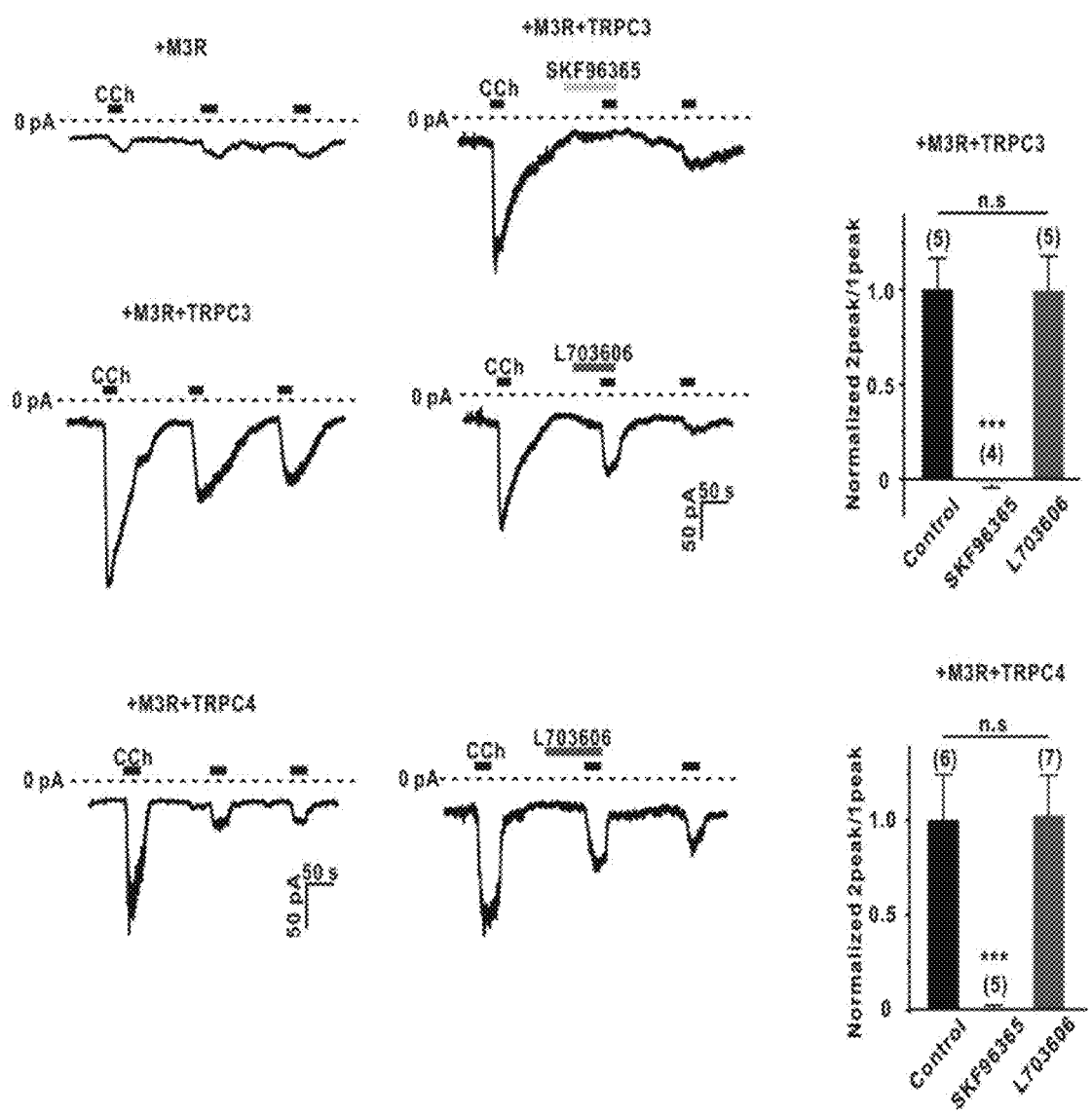
FIGS. 5A and 5B illustrate views which identify NALCN-specific inhibitory activity of L703606, in which it is identified that an inward current is activated by CCh stimulus despite treatment with L703606 in HEK293T cells that have been transfected with M3R and a TRPC channel.
Figure 5B:
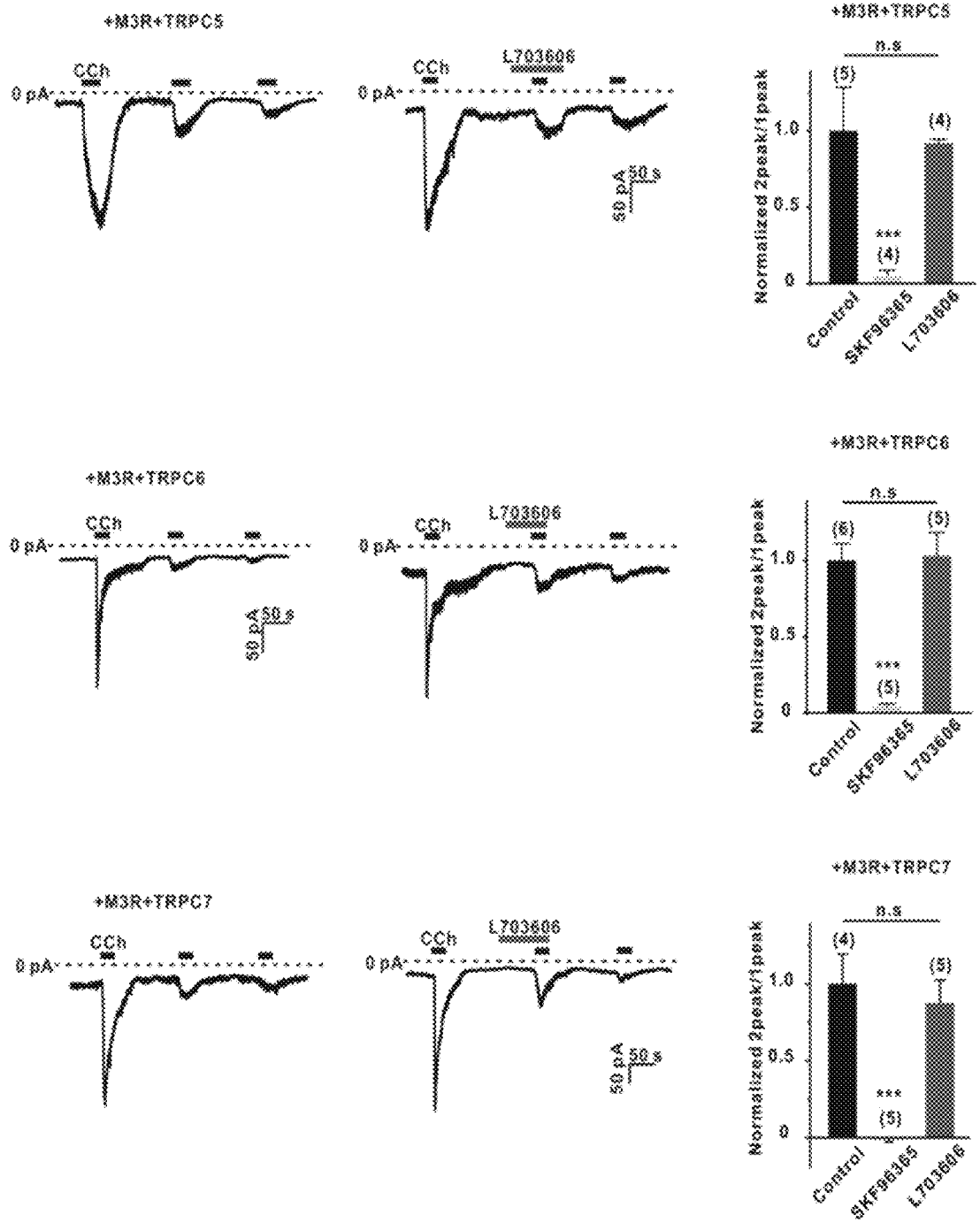

As a result, as shown in FIGS. 5A and 5B, in a case where SKF96365, which is a non-selective inhibitor of a TRPC channel, is treated under a holding potential of −60 mV, a CCh-induced inward current was not created at all, from which it was identified that the current activated by M3R is caused by the TRPC channel. Besides, in a case of being treated with L703606, a CCh-induced inward current was still induced, and a magnitude of the induced current was similar to that of a control. Thus, it was identified that L703606 has no effect on cation channels other than NALCN.

Example 4. Verification of NBQN Derivatives as NALCN Inhibitors

From the above, L703606 for which a NALCN inhibitory effect was identified is one of the NBQN derivatives. In the present example, it was intended to identify that NBQN of the compound L703606 plays a key role in inhibitory effects against NALCN, and NALCN is also effectively inhibited by other NBQN derivatives. Accordingly, treatment with CP96345 or maropitant which has, as a common central structure, NBQN with an unsubstituted or substituted benzyl group was performed instead of treatment with L703606, to identify a degree of decrease in inward current induced by CCh. In addition, treatment with CP99994 or L733060 which is known as an inhibitor of NK-1 receptor similarly to the above compounds but has a different central structure was performed to identify whether these compounds are capable of functioning to inhibit a CCh-induced inward current. Information on the compounds used is shown in Table 2 below.

TABLE 2

| | | |
|---|---|---|
| L703606 | 2-(Diphenylmethyl)-N-(2-iodobenzyl)quinuclidin-3-amine | |
| CP96345 | 2-(Diphenylmethyl)-N-(2-methoxybenzyl)quinuclidin-3-amine | |
| Maropitant | (2S,3S)-2-(Diphenylmethyl)-N-[2-methoxy-5-(2-methyl-2-propanyl)benzyl]quinuclidin-3-amine | |

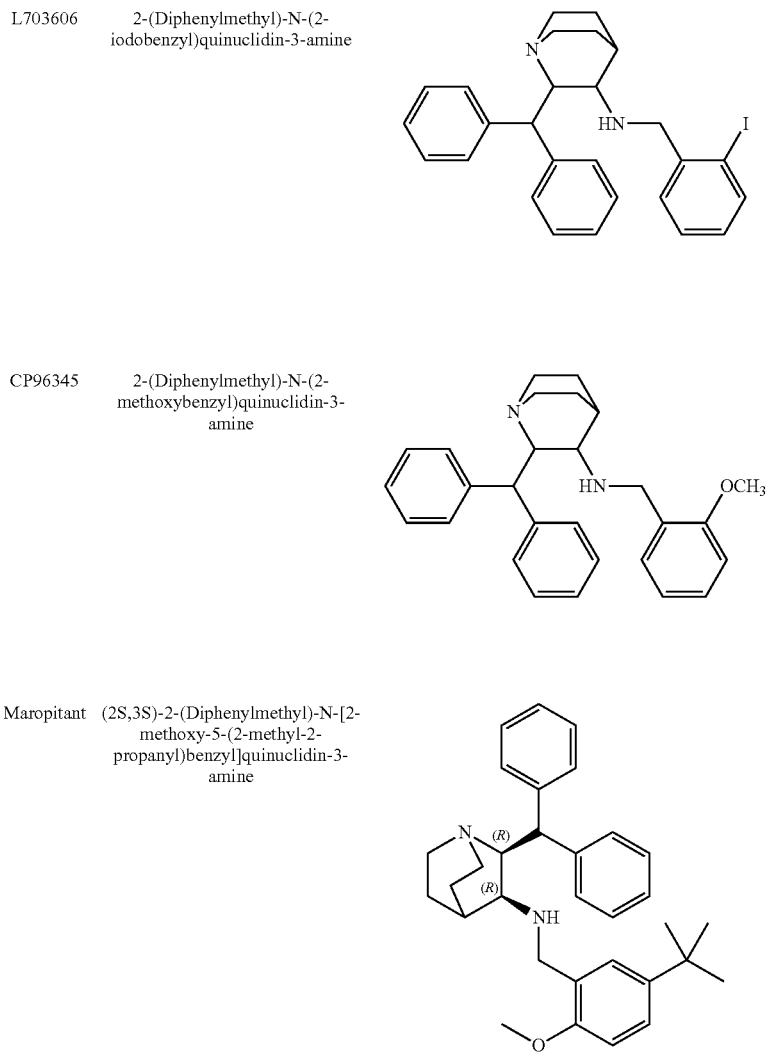

TABLE 2-continued

| | | |
|---|---|---|
| CP99994 | (2S,3S)-N-[(2-methoxyphenyl)methyl]-2-phenylpiperidin-3-amine | 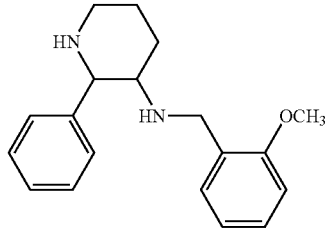 [SMILES: COc1ccccc1CNC1CCCNC1c1ccccc1] |
| L733060 | (2S,3S)-3-[3,5-Bis(trifluoromethyl)benzyl]methoxy-2-phenylpiperidine | 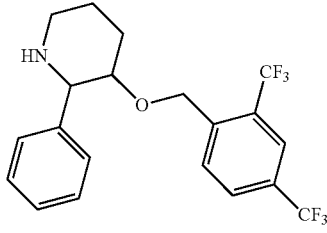 [SMILES: FC(F)(F)c1ccc(COC2CCCNC2c2ccccc2)c(C(F)(F)F)c1] |

Figure 6:
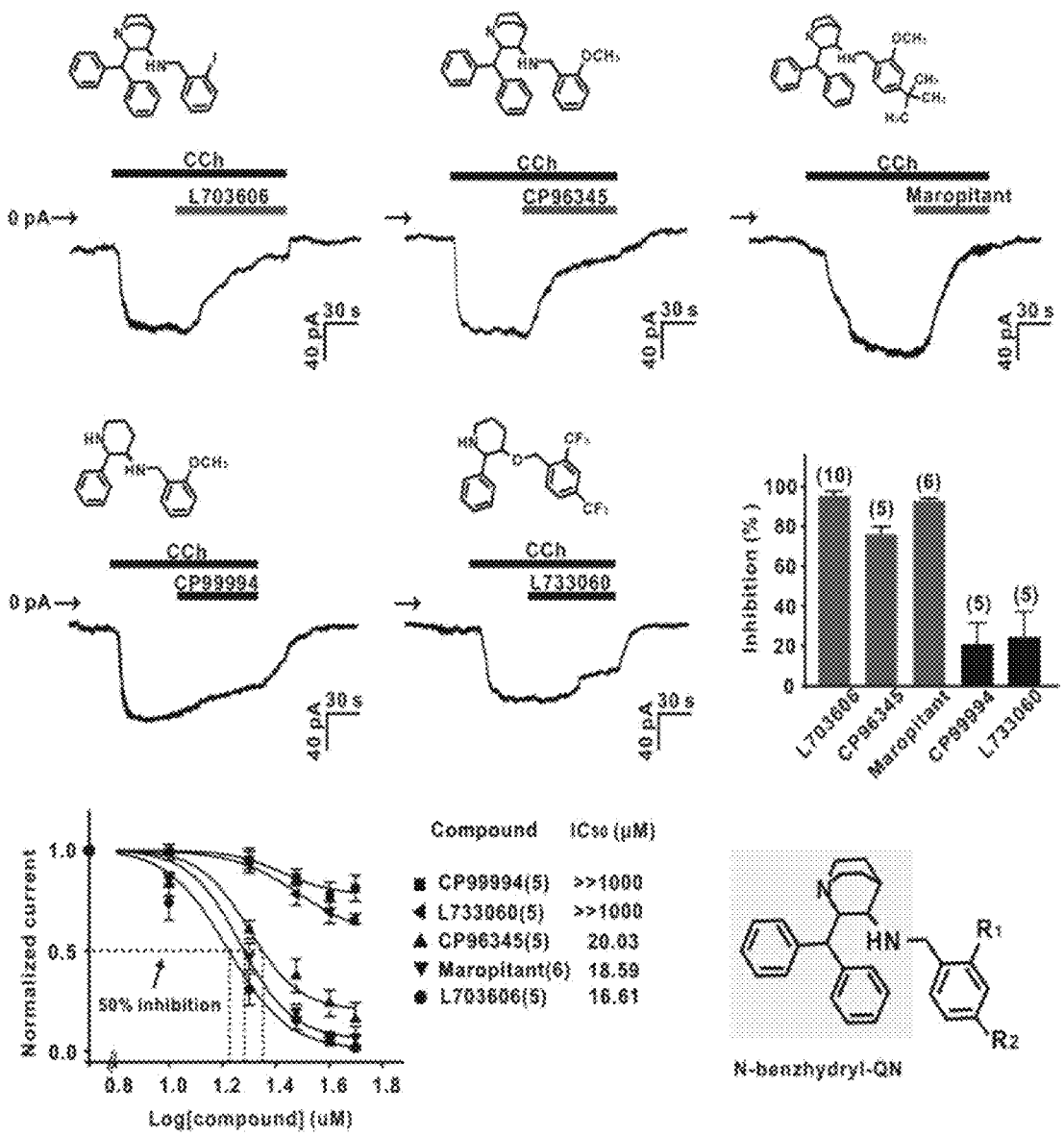
FIG. 6 illustrates views which identify that L733060 and CP99994 have no effect on flow of ions caused by NALCN, and identify that maropitant and CP96345 having the same NBQN skeleton as L703606 effectively inhibit activation of NALCN, indicating that NBQN has a structure that plays a key role in inhibiting NALCN.

As a result, as shown in FIG. 6, it was identified that CP99994 and L733060 have an insignificant inhibitory effect on a CCh-induced NALCN current, and L703606, CP96345, and maropitant, which have, as a mother skeleton, NBQN with an unsubstituted or substituted benzyl group, inhibit a CCh-induced NALCN current in a similar fashion. In a case of obtaining a compound concentration which decreases half of a NALCN current, it was possible to identify that the highest inhibitory effect is exhibited by L703606, and the next highest inhibitory effects are exhibited by maropitant and CP96345 in this order.

From the above, it can be seen that a NBQN structure in which a nitrogen atom and a benzhydryl functional group are bound to a quinuclidine skeleton plays a key role in inhibiting NALCN, and can be used as an effective NALCN inhibitor in both neuronal cells and non-neuronal cells.

In the present disclosure, it has been identified that N-benzhydryl quinuclidine (NBQN) derivatives inhibit NALCN-induced sodium ion leak current in dopaminergic neurons and human embryonic kidney-derived cells, inhibit activation of NALCN by neurotransmitters, and rapidly convert NALCN, which has been activated by neurotransmitters, to an inactive state. Accordingly, it can be seen that the NBQN derivatives inhibit activity of NALCN in neuronal cells as well as non-neuronal cells, so that cell excitability can be regulated and excitation of cells caused by chemical and/or physical stimuli can be inhibited. Accordingly, the NBQN derivatives of the present disclosure are expected to be used in various fields such as drug, quasi-drug, cosmetic, and cosmetic material compositions for preventing or treating degenerative cranial nerve diseases and excitatory cranial nerve diseases which develop due to abnormality of NALCN, and diseases such as cancer, metabolic diseases, and heart diseases which can be prevented or treated through regulation of cell excitability.

In addition, in the examples described herein, it has been identified that the NBQN derivatives have no effect on opening and closing of ion channels other than NALCN. Thus, it is expected that the NBQN derivatives will be usefully used, as compositions for specifically inhibiting NALCN, to study function, action, and mechanism of NALCN in the future.

While specific examples have been shown and described above, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects of the present disclosure in each example are to be considered as being applicable to similar features or aspects of the present disclosure in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method for inhibiting a sodium leak channel, comprising:
    treating a cell comprising a mutation of a gene encoding the sodium leak channel with a pharmaceutical composition comprising as an active ingredient N-benzhydryl quinuclidine, a N-benzhydryl quinuclidine derivative represented by the following Formula 1, or a pharmaceutically acceptable salt thereof; and
    detecting and measuring a change of an electrical current through the sodium leak channel in the cell,
    wherein in the following Formula 1, R is an unsubstituted or substituted benzyl group, and
    wherein the N-benzhydryl quinuclidine, a N-benzhydryl quinuclidine derivative or a pharmaceutically acceptable salt thereof inhibits a sodium leak channel in the individual in need thereof:

[Formula 1]

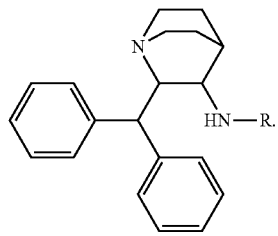

2. The method according to claim 1,
    wherein $R_1$ is hydrogen, halogen, or methoxy, and
    $R_2$ is hydrogen or $C_{1-4}$ alkyl.

3. The method according to claim 1,
    wherein the N-benzhydryl quinuclidine derivative is
    2-(diphenylmethyl)-N-(2-iodobenzyl)quinuclidin-3-amine,
    2-(diphenylmethyl)-N-(2-methoxybenzyl)quinuclidin-3-amine, or
    (2S,3S)-2-(diphenylmethyl)-N-[2-methoxy-5-(2-methyl-2-propanyl)benzyl]quinuclidin-3-amine.

4. The method according to claim 1, wherein the cell is obtained from a subject suffering from a disease resulting from abnormality of the sodium leak channel.

5. The method according to claim 4, wherein the disease is one or more diseases selected from the group consisting of infantile neuroaxonal dystrophy (INAD), neurodevelopmental autosomal syndromes with severe hypotonia, speech impairment, cognitive delay, cervical dystonia, pancreatic cancer, non-small cell lung cancer, glioblastoma, 13q deletion syndrome, restless legs syndrome, and autism.

6. A method for treating a disease resulting from abnormality of sodium leak channels, comprising:
    administering, to an individual with the disease resulting from abnormality of sodium leak channels, a pharmaceutical composition comprising as an active ingredient N-benzhydryl quinuclidine, a N-benzhydryl quinuclidine derivative represented by the following Formula 1, or a pharmaceutically acceptable salt thereof; and
    detecting and measuring a change of an electrical current through the sodium leak channel to confirm inhibition of the sodium leak channel, wherein in the following Formula 1, R is an unsubstituted or substituted benzyl group, wherein the disease is one or more diseases selected from the group consisting of infantile neuroaxonal dystrophy (INAD), neurodevelopmental autosomal syndromes with severe hypotonia, speech impairment, cognitive delay, cervical dystonia, pancreatic cancer, non-small cell lung cancer, glioblastoma, 13q deletion syndrome, restless legs syndrome, and autism:

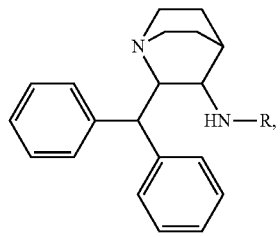

[Formula 1]

and wherein the abnormality of sodium leak channels is caused by a mutation of a gene encoding the sodium leak channel.

7. The method according to claim 6, wherein
R₁ is hydrogen, halogen, or methoxy, and
R₂ is hydrogen or C₁₋₄ alkyl.

8. The method according to claim 6,
wherein the N-benzhydryl quinuclidine derivative is 2-(diphenylmethyl) -N-(2-iodobenzyl)quinuclidin-3-amine, 2-(diphenylmethyl)-N-(2-methoxybenzyl)quinuclidin-3-amine, or (2S,3S)-2-(diphenylmethyl)-N-[2-methoxy-5-(2-methyl-2-propanyl)benzyl] quinuclidin-3- amine.

9. The method according to claim 6,
wherein the disease resulting from abnormality of sodium leak channel is one or more diseases selected from the group consisting of sodium leak channel is one or more diseases selected from the group consisting of infantile neuroaxonal dystrophy (INAD), neurodevelopmental autosomal syndromes with severe hypotonia, speech impairment, cognitive delay, cervical dystonia, pancreatic cancer, non-small cell lung cancer, glioblastoma, 13q deletion syndrome, restless legs syndrome, and autism.

10. A method for inhibiting a sodium leak channel, comprising:
treating a cell comprising a mutation of a gene encoding the sodium leak channel or an with a pharmaceutical composition comprising as an active ingredient N-benzhydryl quinuclidine, a N-benzhydryl quinuclidine derivative represented by the following Formula 1, or a pharmaceutically acceptable salt thereof; and
detecting and measuring a change of an electrical current through the sodium leak channel in the cell:

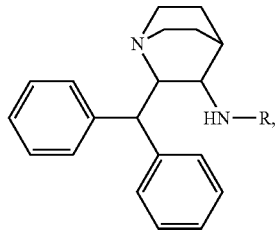

[Formula 1]

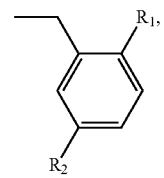

wherein R is wherein R₁ is hydrogen, halogen, C₁₋₄ alkyl, C₁₋₄ haloalkyl, or C₁₋₄ alkoxy, and R₂ is hydrogen, halogen, or C₁₋₄ haloalkyl, and wherein the N-benzhydryl quinuclidine, a N-benzhydryl quinuclidine derivative or a pharmaceutically acceptable salt thereof inhibits the sodium leak channel.

11. The method according to claim 10, wherein
R₁ is hydrogen, halogen, or methoxy, and
R₂ is hydrogen.

12. The method according to claim 10,
wherein the N-benzhydryl quinuclidine derivative is 2-(diphenylmethyl)-N-(2-iodobenzyl)quinuclidin-3-amine, or 2-(diphenylmethyl)-N-(2-methoxybenzyl) quinuclidin-3-amine.

13. The method according to claim 10, wherein the cell is obtained from a subject suffering from a disease resulting from abnormality of the sodium leak channel.

14. The method according to claim 13, wherein the disease is one or more diseases selected from the group consisting of infantile neuroaxonal dystrophy (INAD), neurodevelopmental autosomal syndromes with severe hypotonia, speech impairment, cognitive delay, cervical dystonia, pancreatic cancer, non-small cell lung cancer, glioblastoma, 13q deletion syndrome, restless legs syndrome, and autism.

* * * * *